United States Patent [19]
Fishman et al.

[11] Patent Number: 5,962,331
[45] Date of Patent: Oct. 5, 1999

[54] CELL GROWTH REGULATOR

[75] Inventors: Pnina Fishman, Herzliya, Israel; Guirguis Raouf, Rockville, Md.

[73] Assignee: Can-Fite Technologies Ltd., Tel-Aviv, Israel

[21] Appl. No.: 08/531,783

[22] Filed: Sep. 21, 1995

[30] Foreign Application Priority Data

Sep. 22, 1994 [IL] Israel .......................................... 111021

[51] Int. Cl.$^6$ ......................... G01N 33/53; G01N 33/574; A01N 43/04
[52] U.S. Cl. .......................... 436/64; 436/501; 435/7.23; 435/7.21; 435/7.24; 514/23; 514/54
[58] Field of Search ................................ 436/501, 63, 64; 435/7.1, 7.21, 7.23, 7.24; 514/23, 54

[56] References Cited

U.S. PATENT DOCUMENTS

| | | | |
|---|---|---|---|
| 4,708,948 | 11/1987 | Iwata et al. | 514/2 |
| 5,242,692 | 9/1993 | Djaldetti et al. | 530/350 |

OTHER PUBLICATIONS

Svet–Moldavsky, George J., et al., Factor Suppressing Alpha Fetoprotein Production, Journal of the National Cancer Institute, vol. 55, No. 5, (Nov. 1975).

Siegel, Israel, et al., Cytotoxic Effects of Free Fatty Acids on Ascites Tumor Cells, JNCI, vol. 78, No. 2, (Feb. 1987).

Parshley, Mary Stearns, Effect of Inhibitors from Adult Connective Tissue on Growth of a Series of Human Tumors in Vitro, Cancer Research, vol. 25.

Laug, Walter, E., Inhibition of Human Tumor Cell–Associated Fibrinolysis by Vascular Bovine Smooth Muscle Cells, JNCL. vol. 75, No. 2 (Aug. 1985).

Bohmer, Frank–D, et al., A Polypeptide Growth Inhibitor Isolated From Lactating Bovine Mammary Gland (MDGI) is a Lipid–Carrying Protein, Journal of Cellular Biochemistry 38:199–204 (1988).

S.A. Hoffman, The Influence of Exercise on the Growth of Transplated Rat Tumors, vol. 22, Jun. 1962, pp. 597–599.

Vickie E. Baracos, Exercise Inhibits Progressive Growth of the Morris Hepatoma 7777 in Male and Female Rats, Aug. 31, 1988, pp. 864–870.

Albert Szent–Gyorigyi, Cancer Therapy: A Possible New Approach, Science, vol. 140, May 1963, pp. 1391–1392.

T. Namba, Inhibition of Ehrlich Ascites Tumour Cells by Skeletal Muscle Extracts, Jan. 8, 1968, pp. 294–301.

*Primary Examiner*—Toni R. Scheiner
*Attorney, Agent, or Firm*—Blank Rome Comisky & McCauley LLP

[57] ABSTRACT

A substance secreted or shed by muscle cells and white blood cells is disclosed. This novel substance is active in inhibiting proliferation of tumor cells and proliferation of stimulated lymphocytes. The substance does not inhibit proliferation of normal cells. This substance is used in accordance with the invention for treatment or prevention of cancer and the level of said substance in a body fluid or in a fluid conditioned by the growth therein of cells withdrawn from the individual, is used for the diagnosis of cancer or the level of risk of the individual of developing cancer.

20 Claims, 19 Drawing Sheets

CELL GROWTH REGULATOR

FIELD OF TERM INVENTION

The present invention is generally in the field of human and veterinary medicine and concerns novel substances which effect growth and proliferation of cells. The present invention is also concerned with uses of the substances in prevention or therapy of diseases. The invention further concerns a method of diagnosis of diseases or screening for individuals which are prone to or which have a predisposition to develop a disease.

GLOSSARY

For the purpose of streamlining the description herein, use will be made with several coined terms. Some of these terms and the manner in which they should be understood in the context of the present writing, are the following:

"Cell Growth Regulator (G)"—an agent effecting growth or proliferation of cells. The effect of the GR on growth or proliferation may either be in promoting growth or proliferation of cells, or in inhibiting growth or proliferation of cells.

"Endogenous GR (EGR)"—an agent secreted by or shed from a call within the body which effects growth or proliferation of the same cell or of other cells within the body, "Cytostatic GR/EGR"—a GR/EGR having an effect in halting or considerably slowing growth or proliferation of cells, this being substantially without any cell destruction. Cytostatic EGRs typically act by arresting the cell cycle in one of the cell cycle phases.

"Low Molecular Weight-EGR (LMW-EGR)"—an EGR which has a molecular weight below about 3,000 Daltons.

"Muscle Factor (MF)"—an LMW-EGR secreted by or shed from muscle cells.

"White Blood Cell Factor (WBF)"—an LMW-EGR secreted by or shed from white blood cells.

"Source Cell"—cell which secretes or sheds the EGR.

"Target Cell"—cell which is effected by the EGR.

"Conditioned Medium (CM)"—a medium conditioned by the growth therein of source cells. A CM thus comprises the EGR secreted by the source cells.

"Muscle Cell CM" and "White Blood Cell CM"—a medium conditioned by the growth therein of muscle cells and white blood cells, respectively. The muscle cell CM and the White Blood Cells CM, respectively comprise the MF and the WBF.

The above terms should be construed and understood with reference also to the description below.

BACKGROUND OF THE INVENTION

There is a heavy body of research involved the discovery, characterization, biological testing and clinical development of EGRs known as "cytokines". All cytokines discovered to date are proteinaceous substances having a molecular weight in the range of several thousand Daltons to several tens of thousands of Daltons. Cytokines, although having different source and target cells and have different mode of activities, share a common denominator in that all are proteinaceous substances.

It has been reported that physical exercise significantly inhibits growth and progression of tumors in experimental animals (S. A. Hoffman et al., 1962, Cancer Res. 22:597–599;V. E. Baracos, 1989, Chem. J. Physiol. Pharmacol., 67:864–870). A. Szent-Gyorgyi, et al., (1963, Science, 140:1391–1392) reported that extracts of several tissues including thymus, aorta, muscle and tendon contain two substances, one promoting growth of ascites tumors in mice (termed by them "Promine") and the other inhibiting such growth (termed by them "Retine"). The retine was described there as a small molecular weight substance, relatively unstable as it decomposes at room temperature, in about a week. Furthermore, based on its mode of isolation, the substance appeared to be lipophilic. Inhibition of ascites tumor cells by muscle cell extracts has also been described by T. Namba et al., (1968, British J. of Exp. Pathol. 49:294–301) and the inhibitory activity found in the muscle extract was dialyzable through silicon membrane. The activity was affected by heating of the extract although no effect of heating was found in the dialyzate.

E. Watta et at (U.S. Pat. No. 4,708,948) disclosed a high molecular weight. polypeptide which inhibits tumor growth obtainable also from muscle tissue. M. Djaldetti et al. (U.S. Pat. No. 5,242,692) disclosed a factor derived from muscle cells which inhibits the proliferation of tumor cells. This factor, which was isolated from the supernatant of a muscle cell culture, was found to have an apparent molecular weight determined by gel electrophoresis, in the range of 25,000–30,000 Daltons.

SUMMARY OF THE INVENTION

The present invention is based on the discovery of novel substances secreted, shedded or produced by either muscle cells or white blood cells which are biologically active in inhibiting proliferation of tumor cells, substantially without affecting proliferation of normal, non tumorous cells. In addition, these substances were also found to be effective in inhibiting proliferation of stimulated immune cells.

Accordingly, the present invention provides, by one of its aspects, a substantially purified cell growth regulator, which is either:

(a) an LMW-EGR, being an agent having the following characteristics:
  i. it is produced by, secreted from, or shed by cells, particularly muscle cells or white blood cells,
  ii. it has a molecular weight of less than about 3,000 Daltons,
  iii. it is not proteinaceous,
  iv. it is soluble in water,
  v. it is heat stable, and
  vi. it is biological active in inhibiting proliferation of cells, particularly it inhibiting proliferation of tumor cells or proliferation of stimulated lymphocytes; or (b) an agent which is a derivative of the agent under (a) and which is biologically active in inhibiting proliferation of cells.

By another of its aspects the present invention provides use of said substance in the prevention or therapy of diseases. In accordance with this aspect, there is provided a method for the prevention of a disease or disorder which comprises administering to a subject in need an effective amount of said GR. Given the GR's mode of activity in Inhibiting proliferation, it will typically be administered to the subject periodically over a period of time. Further, In accordance with this aspect, there is provided a composition comprising an amount of said GR. The composition may be a pharmaceutical composition comprising a therapeutically effective amount of said GR, together with a pharmaceutically acceptable carrier or diluent. The pharmaceutical composition may be formulated so as to be rendered useful for prevention of a disease or disorder or formulated so as to be rendered useful for therapy of a disease or disorder. The composition may also be a non-prescription composition; e.g. a neutraceutical composition, a food additive, a health food preparation, etc Finally, also provided in accordance with this aspect is the use of said GR for the preparation of such compositions.

Particularly preferred is the use of said GR for the treatment or prevention of cancer, or for inhibiting (eliminating or reducing) activity of stimulated lymphocytes within the framework of treatment or prevention of a variety of conditions resulting from a hyperactive immune system, e.g. treatment intended to counter organ rejection, treatment of autoimmune diseases, etc.

In accordance with a further aspect of the invention, there is provided a method for the diagnoses of cancer or a cancerous state of an individual, or for the screening for individuals which are prone or have a predisposition to develop cancer comprising determining level of said LMW-EGR in a body fluid obtained from said individual, or in a supernatant of a culture of cells obtained from said individual.

An additional aspect of the present invention is a process for the preparation of the GR of the invention based on a purification of active fractions of appropriate conditioned media.

DESCRIPTION OF THE INVENTION

The present invention is based on the discovery of novel EGRs which have a low molecular weight. The term "low molecular weight", should be understood to be a molecular weight, as determined by ultrafiltration, which is less than about 3,000 Daltons, particularly less than about 2,000 Daltons, and preferably of, or less than about 500 Daltons. It is clear to the artisan that these molecular weights are approximations and cannot be regarded as exact figures.

The LMW-EGRs of the invention were found to be non-proteinaceous, i.e. they are neither proteins, nor peptides, nor any other substance having a protein or a peptide moiety which plays a role in its biological activity. (The findings of the present invention cannot rule out the possibility that the LMW-EGR can exist in a form in which it is bound or complexed to a peptide or a protein moiety, which plays no role or has only a limited role in the LMW-EGR's activity as a growth regulator).

In accordance with the invention, LMW-EGRs were obtained to date from a muscle cells' CM and from a white blood cells' CM. It is believed, however, that LMW-EGRs in accordance with the invention may be obtained also from other sources. The present invention is thus not limited to the MF and the WBF. On the contrary, equipped with the knowledge gained by the findings in accordance with the invention and by employing standard skills and knowledge available to him, the artisan will have no difficulties in finding other LMW-EGRs, which fall within the scone of the present invention.

The MF and WBF were: found to be tumor-specific cytostatic EGRs. They have a unique biological activity in that they specifically inhibit growth and proliferation of tumor cells without having any noticeable effect on normal, non tumorigenic, cells. In addition, both the MF and WBF were found to be tumor non-specific (i.e., effective in inhibiting growth and proliferation of a variety of tumor cells) and species nonspecific (showing activity in inhibiting growth and proliferation of tumor cells from a variety of animal species).

In other words, the MF and WBF have a broad spectrum of activity in inhibiting growth and proliferation of cancer cells. Furthermore, the findings in accordance with the invention signify also that an MF or WBF derived from one animal species, particularly mammal, may be used in cancer treatment of an animal of another species, particularly mammalian.

It should be pointed out although the ME and the WBF were found to be cytostatic agents, it is possible that they may have some destructive effect on cells, particularly following a prolonged exposure. For example, after a prolonged exposure to the MF or the WBF, as well as to their derivatives, the target tumor cells may eventually die, e.g. as a result of apoptosis.

In addition to their activity in inhibiting growth and proliferation of tumor cells, the ME and WBF were found to be active also in inhibiting lymphocyte's proliferation as evidenced by the inhibition of lymphocyte's response to a mitogen and of a mixed lymphocyte reaction (MLR), meaning that the GRs of the invention may have an immunosuppressive activity.

It is clear that once an LMW-EGR is isolated from one species, it is possible to find an homologous LMW-EGR from another species. For example, until now the MF obtained in accordance with the invention We from rat and human origin. There is no doubt that it is possible to obtain also homologous MFs from other, particularly mammalian, species.

Similarly, the WBF obtained to date in accordance with the invention is of a human origin. There is no doubt that homologous WBFs from other species, particularly mammalian, may also be obtained. The present invention also encompasses such homologs.

The GR of the invention may be a single molecule, a group of molecules operating together in an additive or synergistic manner in affecting growth and proliferation of cells, or a molecular complex having such activity.

Once isolated, it is possible to prepare derivatives, e.g. by chemical modification, of the LMW-EGR which will possess a biological activity which is similar to that of the LMW-EGR. Derivatives having a similar biological activity to an LMW-EGR or homologs to such an LMW-EGR can be identified, for examples by employing the same biological tests used to characterize the LMW-EGR. For example, in the case of the MF and WBF, which are active in inhibiting growth or proliferation of tumor cells, derivatives and homologs can be found by testing synthetic derivatives or fractionated CM from other species, as the case may be, for activity in inhibiting growth or proliferation of tumor cells grown in vitro or by the ability to inhibit the, MLR. The artisan, will no doubt be capable of selecting the appropriate biological assay in each case.

The derivative may be a molecule having a similar molecular structure to said LMW-EGR, but in which one or more chemical groups has been substituted by another; a reduction or oxidization product of said LMW-EGR; etc.

The GR of the invention may be used for a variety of therapeutic purposes wherein it will be administered in a therapeutically effective amount to a subject in need. One preferred therapeutic indication for which said GR may be used, is in the treatment or prevention of cancer. For treatment, the OR may be administered to individuals having a cancer history, e.g., in order to inhibit cancer recurrence. Such a treatment will typically be a follow-up of an initial treatment intended to remove or destroy the cancer, such as chemotherapy, radiation therapy or surgery. For prevention, said GR may be administered to cancer-free individuals or to individuals prior to the diagnosis of any cancerous condition, particularly to high risk individuals who are prone or have a predisposition to develop cancer. High risk individuals may be such having a genetic predisposition to develop cancer, e.g. individuals diagnosed as having one of the variety of genes known to be associated with cancer; individuals with a family history of cancer; individuals who are at high risk of developing cancer as a result of exposure to a variety of environmental factors such as irradiation, exposure to carcinogens, etc.; etc.

Given a GRs biological activity which is inhibition of proliferation of target cells, rather than immediate destruction of target cells, the GR will typically be administered periodically over a period of time. However, as already pointed out above, it is possible that following a prolonged arrest of their growth, tumor cells will eventually die so that it will be possible to terminate the treatment after a certain period of time.

Another preferred therapeutic indication of said GR is in inhibiting activity of components of the immune system. Examples are the treatment of autoimmune diseases; use within the framework of transplantation therapy, i.e. treatment following transplantation intended to avoid organ or tissue rejection; etc.

The GRs of the invention were tested in a variety of animal models, including animal models for primary tumors in which a tumor is induced by subcutaneous, intramuscular or intraperitoneal inoculation of tumor cells, as well as animal models for metastasis, in which a tumor is induced by an intravenous inoculation of tumor cells. The GR was found to be effective in inhibiting development of tumors in both classes of models. The GRs were found to be effective in inhibiting tumor development both by parenteral and by oral administration. As known, oral administration is much more physiologically tolerable than parenteral administration and accordingly for treatment or prevention of cancer, particularly in treatment or prevention regimens involving administration of the GR periodically over a prolonged period of time, oral administration route is preferred.

The GR may be formulated into a pharmaceutical composition which will comprise an effective amount of said GR together with a physiologically acceptable carrier which is compatible with said GR. Said GR was found to be soluble in water and accordingly, a physiologically acceptable carrier may be saline, for parenteral administration or may be an edible, aqueous liquid, for oral administration. In addition, for oral administration, the GR. may be formulated into a variety of dosage forms, such as capsules, tablets, etc. Furthermore, the GR may also be lyophilized to be admixed with the carrier or diluent prior to use.

The term "effective amount" as used herein should be understood as an amount sufficient to achieve a desired effect. For example, in case of cancer therapy, an effective amount is an amount of said GR in a given therapeutic regimen which is sufficient to inhibit the growth and proliferation of tumor cells, as evidenced, for example, by a decrease in the rate of occurrence or a decrease in the number of cancer metastasis or a decrease in the rate of cancer related mortality. In tire case of cancer prevention, an effective amount is an amount of said GR. in a given preventive administration regimen, which is sufficient to inhibit the occurrence of primary cancerous growth.

In addition to formulation of the GR into pharmaceutical compositions, the GR of the invention may also be formulated into other types of compositions, e.g. food additive compositions, neutraceutical compositions, non-prescription "health" products, etc.

Experiments performed in accordance with the invention have shown that white blood cells of cancer patients secrete much lower amounts of the LMW-EGR than do white blood cells of normal, healthy individuals. Thus, by determining the level of the LMW-EGR in a body fluid (e.g. serum, urine, etc.), or in a supernatant of a culture of cells, e.g. muscle cells or white blood cells of an individual, it will be possible to diagnose cancer in an individual as well as to obtain an indication of an individual's cancerous state. In addition, determination of the level of the LMW-EGR in a body fluid or in said supernatant, may be a basis for screening for individuals' which are prone or have a predisposition to develop cancel A determination of the level of the LMW-EGR may be preformed by means of a biological assay which involves testing the activity of the body fluid or the supernatant, or the activity of an appropriate fraction thereof, in inhibiting proliferation of tumor cells. In addition to such a biological assay, the presence of the LMW-EGR may also be determined by a number of analytical methods, generally known per se, to the artisan, which include a variety of immunological assays based on the use of LMW-EGR-specific antibodies; assays based on the use of appropriate chemical, e.g. color reagents; spectroscopic assays or assays based on absorption of irradiation, e.g. light absorption; a variety of chromatographic techniques; etc, By another of its aspects the present invention provides a process for the purification of a GR of the invention from a biological source. The process in accordance with this aspect comprises:

(a) growing cells under conditions in which the cells produce, secrete or shed cell growth regulator into their surrounding medium;

(b) collecting supernatant of the cell culture;

(c) separating between a fraction of the supernatant comprising substances of a molecular weight above about 3,000 Daltons and fractions of the supernatant comprising substances of a molecular weight below about 3,000 Daltons, and selecting the latter.

The fractions selected in step (c) may be purified further by a variety of purification techniques, specifically chromatography, e.g. high pressure liquid, chromatography (HPLC).

In the following, the invention will be illustrated by some experiments carried out in accordance with the invention, with occasional reference to the annexed drawings. In these experiments, in vitro and in vivo activity of the MF and WBF is demonstrated. Also described are purification and characterization procedures of the MF. It will no doubt be appreciated by the artisan that this illustration should not be construed as limiting the scope of the invention, but rather as exemplifying the full scope of the invention as defined in the appended claims. The artisan will no doubt be able, based on the above and the following description, to carry out the invention in its full claimed scope.

BRIEF DESCRIPTION OF THE DRAWINGS

In the drawings:

In FIGS. 1A, 1B, 2A, 2B, 3A, 3B, 4 6, 8 and 9, and partially in FIG. 7, the cell perforation was measured by $^3$H-thymidine incorporation, and the ordinate shows the radio activity count. In FIG. 5 and partially in FIG. 7, the proliferation was measured by cell count and the ordinate shows the cell number.

FIGS. 1A and 1B show the effect of a 2,000 Dalton MF ultrafiltrate obtained from a primary culture of newborn rat striated muscle cells, on the proliferation of two tumor cell lines; B16, which is a murine melanoma cell line (FIG. 1A); HTB-38, which is a human adenocarcinoma cell line (FIG. 1B) In this figure, the activity of 3,000 Dalton MF ultrafiltrate is compared to that of the crude conditioned medium ("crude CM").

FIGS. 2A and 2B show the effect of a 3,000 Dalton MF ultrafiltrate derived from a primary culture of newborn rat striated muscle cells, on two types of normal, non-tumor cells: rat fibroblast (FIG. 2A); murine bone marrow cells (FIG. 2B).

FIGS. 3A and 3B show the effect of a 3,000 Dalton MF ultrafiltrate derived from a line of rat striated muscle cells— L-8, on the proliferation of two tumor cell lines: B16 (FIG. 3A); MCA-105, murine lung methylcholantrene-induced sarcoma line (FIG. 3B).

FIG. 4 shows the effect of a 3,000 Dalton MF ultrafiltrate derived from L-8 cells, on two normal types of cells: murine bone marrow cells and primary culture of rat fibroblasts.

FIG. 5 shows the effect of a 3,000 Dalton MF ultrafiltrate derived from a primary culture of newborn rat striated muscle cells, on the proliferation of cells of the $Nb_2$-11C rat lymphoma line, in a cell growth assay based on cell counting. It this assay the cells were synchronized in the $G^0/G^1$ phase, 3,000 Dalton MF ultrafiltrate crude CM or a control medium were added and then growl was stimulated by the addition of the hGH.

FIG. 6 shows the effect of a 3,000 Dalton ME ultrafiltrate derived from L-8 cells, on the proliferation of several tumor cell lines. The results in each case are a percent of the control in the respective experiment.

FIG. 7 shows the effect of a 3,000 Dalton MF ultrafiltrate derived from human myoblasts. The proliferation of the B-16 and the K562 cells was determined by means of $^3$H-thymidine incorporation; the proliferation of the NBT cells was determined by way of cell mount.

FIG. 8 shows the effect of a 3,000 Dalton WBF ultrafiltrate derived from human lymphocytes on the proliferation of murine and human tumor cells. The proliferation is shown as a percent of control.

FIG. 9 shows the effect of a 3,000 Dalton MF ultrafiltrate derived fm L-8 cells, on lymphocytes response to PHA and in a mixed lymphocyte reaction (MLR).

FIG. 14a shows the proliferation of the three cell lines, versus control, following exposure to the 3,000 Dalton ultrafiltrate; and FIG. 14b shows the scattered results given as a percent of inhibition (inhibition being the reciprocal of proliferation— 100% proliferation being 0% inhibition, etc. (results of more than 100% proliferation were also given a score of 0%).

FIGS. 16 and 17 show activity of various fractions eluted, in two different runs, from a preparative RP-HPLC (C-18) column, in inhibiting proliferation of $NB_2$ cells. The solutions which were fed into the columns were either a 3,000 Dalton MF ultrafiltrate derived from L-8 cells (in PBS) or a control PBS solution. In FIG. 16, MF containing solution— empty circles (○); control PBS solution—filled circles (●). In FIG. 17, MF containing solution—filled triangles (▼); control PBS solution—filled circles (●).

FIG. 18 shows the activity of various fractions eluted from analytical RP-HPLC (C-18) column, in inhibiting proliferation of $NB_2$ cells. The solution which was fed into this column consisted of a pool of fractions 5 and 6 from FIG. 16. MF solution—filled circles (●); control—empty circles (○).

FIG. 19 shows the activity of various fractions eluted from a superdex column in inhibiting proliferation of $Nb_2$ calls. The solution which was fed into the column was a pooled solution from the eluate of FIG. 17 consisting of 250 ml of tubes 9–10, 520 ml of tubes 10–11 and 600 ml of factions 11–12.

FIG. 20 shows the activity of various fractions eluted from an analytical RP-HPLC column in inhibiting proliferation of $Nb_2$ cells. The solution fed into the column was a pool of tubes 6–12 of FIG. 17. MF solution—filled squares (■) control, PBS solution—empty circles (○).

FIG. 21 shows the activity of various fractions eluted from a size exclusion (SE) column in inhibiting proliferation of $Nb_2$ cells. The solutions which were fed into the column were different fractions eluted from the preparative RP-HPLC column shown in FIG, 17: Fraction "A", Tubes 6–8—empty circles (○); Fraction "B", Tubes 8–10—filled circles (●); Fraction "C", Tubes 10–12—empty triangles (∇); and Fraction "D", Tubes 12–14 filled triangles (▼).

FIG. 22A shows results of the following fed solutions: tubes 28–30 of Fraction C—empty circles (○); tubes 22—23 of Faction C—filled circles (●); tubes 29–33 of Fraction B—empty triangles—(∇); and FIG. 22B shows results of the following fed solutions: tubes 31–32 of Fraction C—filled circles (●); tubes 23–26 of Fraction C—empty circles (○); tubes 29–33 of Fraction B—empty triangles (∇).

DETAILED DESCRIPTION OF THE INVENTION

Figure 1A:
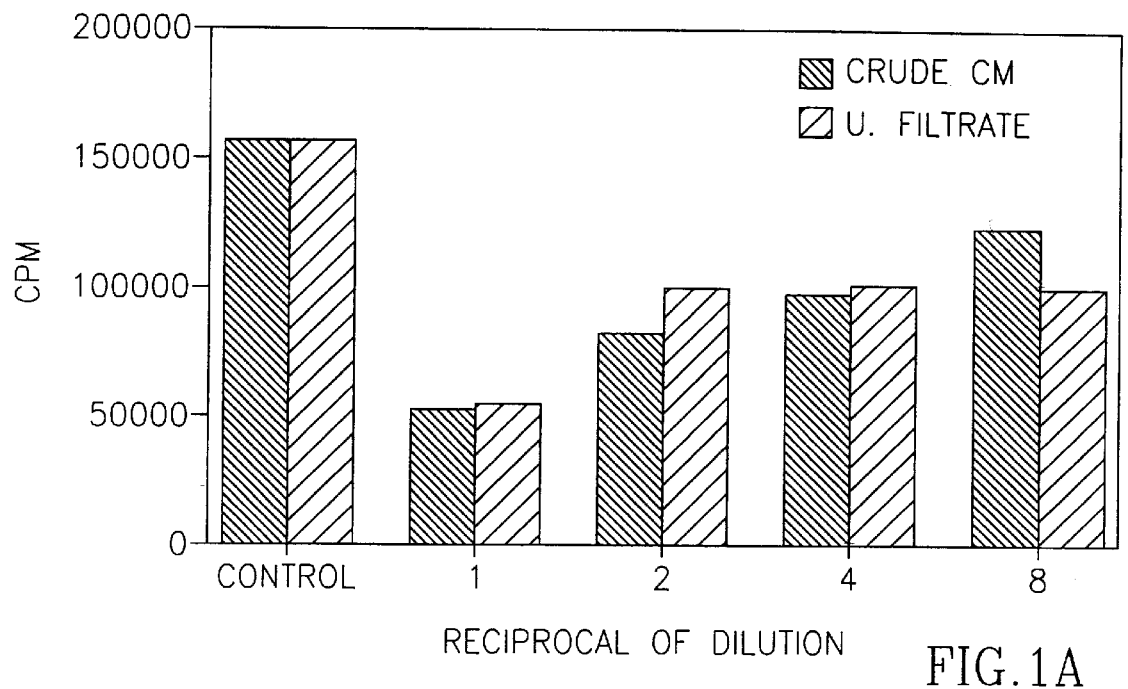
FIGS. 1A, 1B, 2A, 2B, 3A, 3B, 4, 5, 6, 7, 8 and 9 show the effect of the MF or WBF as contained in the filtrate of a muscle cell CM or a white blood cell CM, filtered though a membrane having a molecular cut-off of 3,000 Daltons (such a filtrate will be referred to herein as f "3,000 Dalton MF ultrafiltrate" and "3,000 Dalton WBF ultrafiltrate", respectively). In the figures, cells were grown in 96 microwell plate and incubated with 3,000 Dalton MF filtrate, at several dilutions ("1"- undiluted, "2"- two-fold dilutions, etc.). In all the experiments a non-condition medium served as control.

In the following reference will at times be made to "MF" or "WBF" in discussing the activity of active fractions obtained from a muscle cell CM and a white blood cell CM. It should be understood, that it is possible that these two CMs contain more than one factor having the activities described below. In fact, the HPLC fractionation results obtained in accordance with the invention, some of which are shown below, may be explained in this manner (although other explanations axe also possible). Thus, for example, it is possible that the muscle cell CM contains more tan one factor which has a tumor growth inhibitory effect. Thus, for example, reference made at times to "the MF", etc., should not be construed as meaning the muscle CM contains only a single LMW-EGR, as the muscle cell CM could in fact contain more than one substance all of which could be termed "MF".

1. Conditioned Medium

MF

MF was obtained from conditioned media (CM) of three types of muscle cell preparations:

1.1.1 Primary cultures of newborn rat muscles

Muscles from the hind legs of 24–48 hrs old newborn rats, were separated and minced into small pieces. Following trypsinization with 0.25% trypsinversan solution, cells were preplated in tissue culture dishes to remove the fibroblasts and monocytes. The cells were counted and seeded in enriched Dulbeco modified Eagle medium (DMEM). Five days later, the cultures contained contracting muscle cells. The medium was then discarded and RPMI or PBS medium was added. The cells were incubated in the RPMI medium for 24 hrs and in the PBS for 8 or 24 hrs. The supernatant was then collected, centrifuged and kept, until further processing, in the refrigerator at −20° C.

1.1.2 Rat muscle cell line (L-8)

L-8 line (obtainable from the American Type Culture Collection—ATCC, designation CRL 1769) is a newborn rat skeletal muscle myoblast lie which comprises undifferentiated myoblasts that proliferate without the addition of growth factors L-8 cells were seeded in culture dishes and were grown in an RPMI medium (this medium will be termed hereinbelow as RPMI) containing 4% glucose. 3 days after splitting the culture supernatant was discarded, and replaced with either RPMI or with phosphate buffered saline (PBS) followed by further incubation for 24 hours. The supernatants were then collected and if not immediately further processed, were kept in the refrigerator at −20° C.

1.1.3 Human Myoblasts

Human myoblasts obtained from human biopsy were cultured in rotating culture flasks until confluence (see U.S. Pat. No. 5,130,441). The culture medium was removed and replaced by either a DMEM or a PBS solution, and the cells were further incubated in the solutions for 24 hours. Supernatant was then collected, and the cells were separated therefrom by centrifugation.

1.2 WBF

WBE was obtained from a conditioned medium of mononuclear cells. Mononuclear cells were isolated from venus blood, as follows; 20 ml of Venus blood was withdrawn from a human donor with a heparinized syringe. The heparinized blood was diluted 1:1 with PBS, layered onto 15 ml of Ficoll-Hypaque™ (Pharmacia, Sweden) or Histopaque™ (Sigma, St. Louis, U.S.A.) and centrifuged at 400×g for 30 minutes. The interface containing the mononuclear cells was collected and washed three times with PBS.

$2 \times 10^6$/ml mononuclear cells were suspended in PBS and incubated at 37° C. in a humidified atmosphere of 5% $CO_2$, 95% air for 48 hours. The cell suspension was then centrifuged and the supernatant was collected.

2. Ultrafiltration

The CM obtained from the above sources was subjected to ultrafiltration using filters having molecular cut-offs of 500, 2,000, 3,000 and 10,000 Daltons (Centricon™, Amicon, U.S.A.).

The MF was found to be present in the ultrafiltrate through the membranes having molecular cut-offs of 10,000, 3,000, 2,000 daltons, as well as in the ultrafiltrate of the membrane having a molecular cut-off of 500 daltons as will be shown further below. The WBF was ultrafiltered through a membrane having a molecular cut-off of 3,000 Daltons and the ultrafiltrate was found to contain the WBF.

The ultrafiltrate of the muscle cell CM through a filter with a molecular cutoff of 500, 2,000 etc. will be referred to herein as the "500 Dalton MF ultrafiltrate", "2,000 Dalton MF ultrafiltrate", etc.; the ultrafiltrate of the lymphocyte CM through the filters having a molecular cut-off of 3,000 Dalton will be referred to herein as the "3,000 Dalton WBF ultrafiltrate".

3. In vitro inhibition of tumor cell proliferation by MF and WBF 3.1 Methods 3.1.1 Cell lines The effect of MF or WBF in this in vitro assay was tested on several tumor cell lines and several non-tumorous cells. The tested cells were the following:

(a) tumor cell lines:
HT-29 which is an adenocarcinoma cell line derived from human colon (ATCC, designation HTM-38);
MCA-105, which is a murine lung methylcholanthrene-induced sarcoma cell line;
B16-F1, which is a murine melanoma cell line;
SK-28, which is a human melanoma cell line;
K-562, which is a human leukemia cell line;
DA3 cells, which is a breast carcinoma cell line;
MCF-7, which is a breast carcinoma cell line;
$Nb_2$-11C which is a rat lymphoma cell line which is hormone dependent (i.e. growth of these cells requires the addition of a growth hormone) (Gertler et al., 1985 Endocrinol., 116:1636–1644); and
$Nb_2$-SP which is a lactogenic hormone independent rat lymphoma cell line;

(b) non-tumor cells:
murine bone marrow cells;
primary rat fibroblasts; and
IM-9, which is a human lymphocyte cell line.

3.1.2 $^3$H-thymidine incorporation assay

Tester cells (the cells in which the $^3$H-thymidine incorporation was assayed) were seeded in a 96 microwell plate at an initial cell density of $1\times10^4$ cells/microwell, Each microwell contained a mixture of RPMI and a tested solution, which was either a conditioned medium (a muscle cell CM or a white blood cell CM, in either a RPMI or PBS), a fractionated CM, a control RPMI or PBS (i.e. not conditioned), or a fractionated control RPMI or PBS. The results from each tested solution were compared to the corresponding control (e.g. a fractionated tested solution in PBS was compared to a fractionated PBS, etc.). Following 42 hours of incubation at 37° C. each microwell was pulsed with 10 $\mu$C of $^3$H-thymidine, followed by a further incubation of 6 hours with this radioactive marker. The amount of $^3$H-thymidine uptake was then measured in a liquid scintillation counter.

3.1.3 Cell count assay

Cells of the $Nb_2$-11C rat lymphoma cell line were synchronized and cultured as hitherto described (Gertler et al., 1985, Endocrinol, 116:1636–1644) with the exception being that the cells were cultured in RMPI supplemented with 5% fetal calf serum. Synchronization of $Nb_2$-11C cells in the $G_0/G_1$ phase and monitoring of self proliferation was carried out as described earlier (enter et al., supra). Briefly cells were transferred to a horse serum-supplemented medium and incubated overnight. Then the cells were diluted to about $3\times10^5$ cell/ml, and distributed into a plurality of wells, 0.5 ml/well in 24 microwell plates. Then an amount of up to 0.5 ml of the tested solution was added and self-proliferation was initiated by the addition of high to a final concentration of 2 mg/ml. Cells were incubated at 37° C. in a 5% $CO_2$ containing atmosphere, and following incubation fox 72 hours, they were counted in a Coulter-Counter. Each experiment was performed in two repetition.

Cells of the $Nb_2$-SP and the IM-9 cell line were tested in a similar manner.

3.2 Results 3.2.1 MF

Figure 1B:
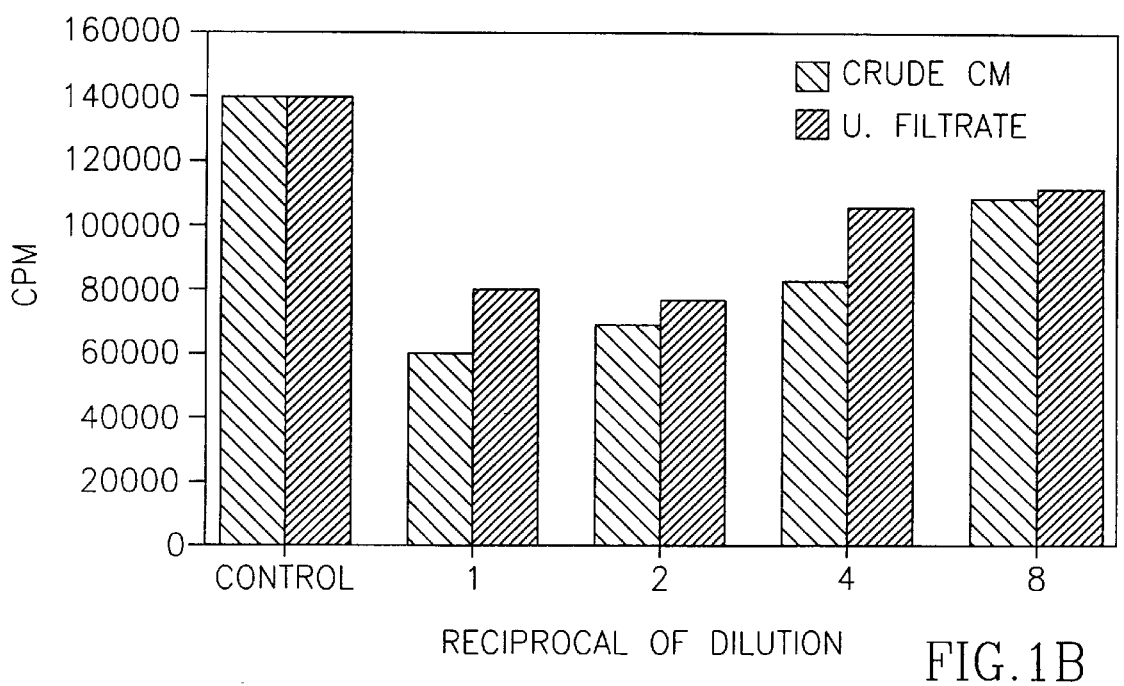
Figure 2A:
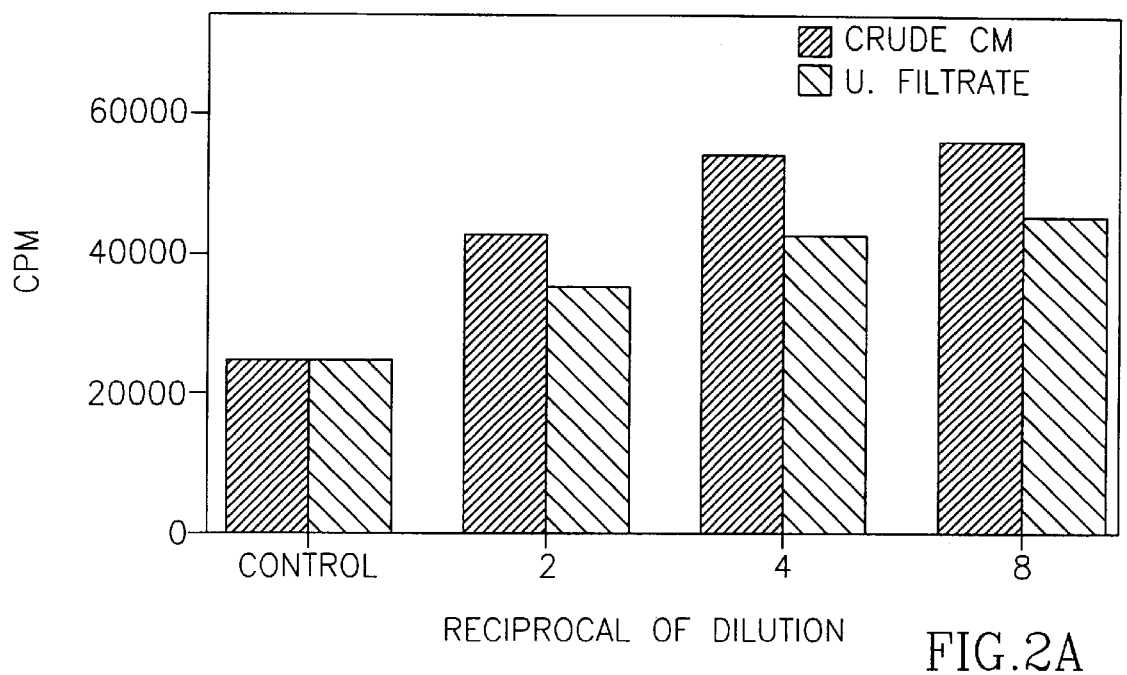
Figure 2B:
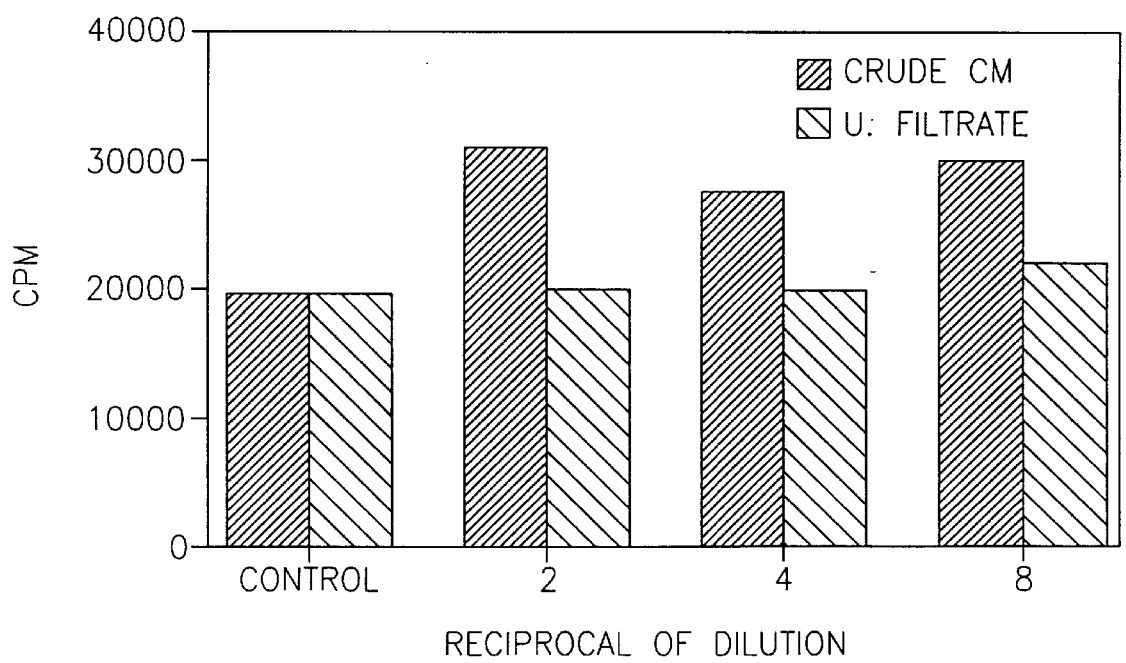
Figure 3A:
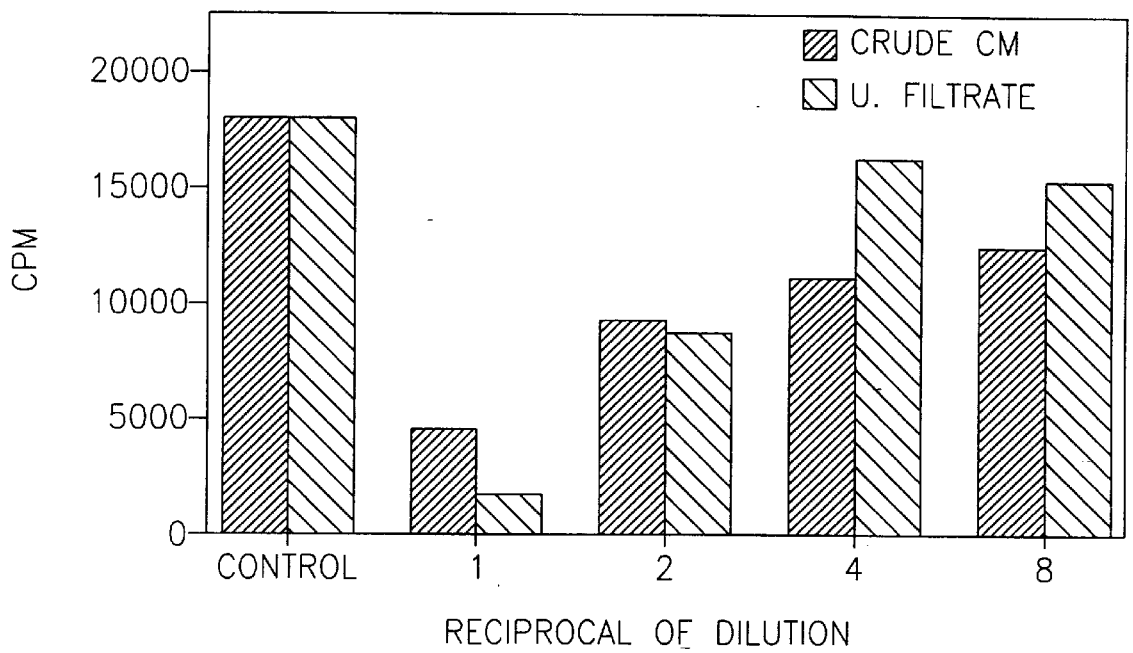
Figure 3B:
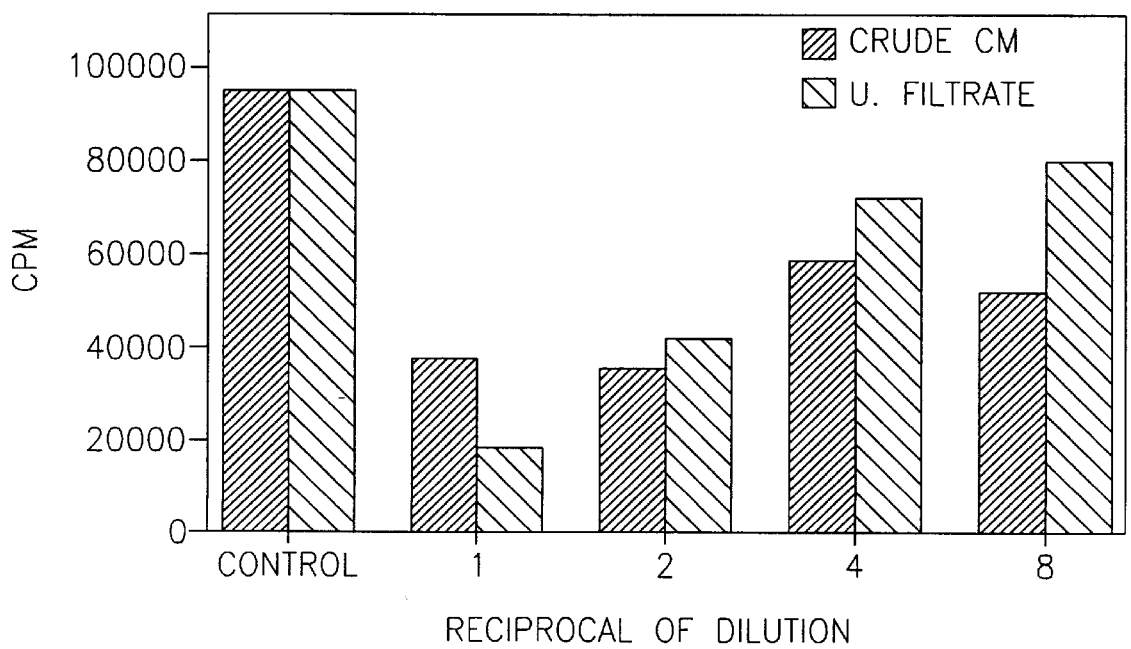
Figure 4:
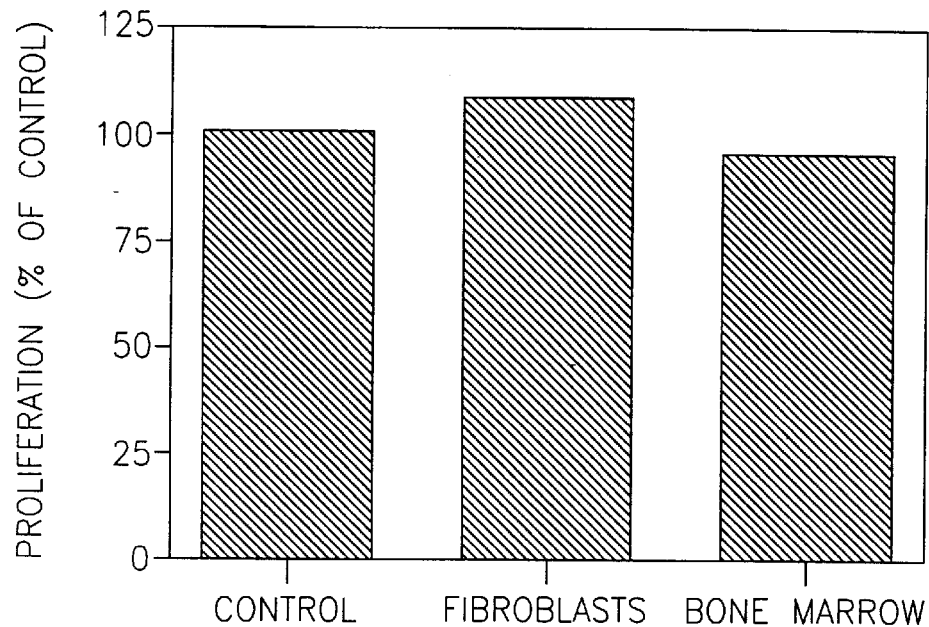

Results with 3,000 Dalton MF ultrafiltrate derived from a primary culture of newborn rat striated muscle cells are shown in FIGS. 1 and 2; results with a 3,000 Dalton MF ultrafiltrate derived from L-8 cells are shown in FIGS. 3 and 4. In each of these figures, the numbers in the Absisca represent a reciprocal of dilution ("1" - undiluted, "2" - two-fold dilution, etc.) and the ordinate shows the radioactivity (counts per minutes—CPM); the control (left column in each ease) was with a non-conditioned medium processed in the same manner as the CM, As can be seen in FIGS. 1 and 3, MF from a primary culture of a rat striated muscle cells (FIG. 1) or from the L-8 striated muscle cell line (FIG. 3), inhibits proliferation of tumor cells while having no such inhibitory effect on normal cells (FIGS. 2 and 4, respectively). Furthermore, it can also be seen that MF filters through the membrane having a molecular cut-off of 3,000 Daltons, as evidenced by the fact that the anti-proliferative activity present in the crude CM is retained in the ultrafiltrate. As can further be seen in FIGS. 1 and 3, the effect of MF decreases with increasing dilution indicating further that this effect is mediated by a specific factor in the ultrafiltrate.

Figure 5:
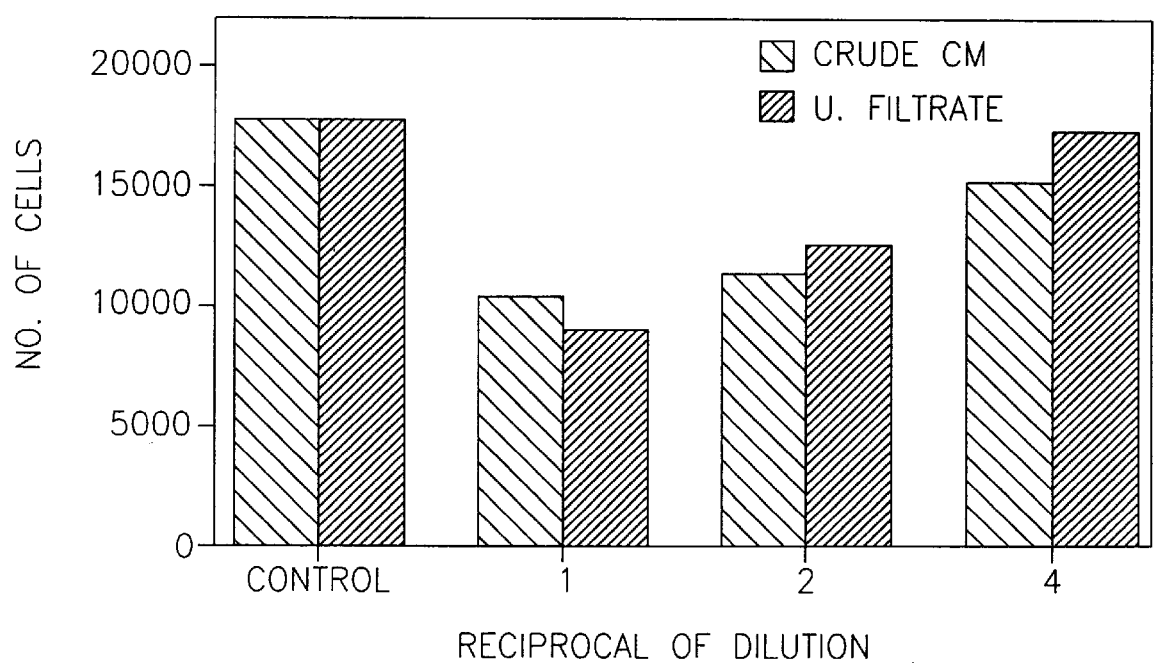

FIG. 5 shows the activity of a crude CM derived from the L-8 line, as well as at a 3,000 Dalton ME ultrafiltrate thereof, both at various dilutions. As can be seen, the crude CM exhibits an anti-proliferating activity which is retained in the ultrafiltrate. Furthermore, the effect decreases with increasing dilution showing, again, that this is a specific, factor-mediated activity.

Figure 6:
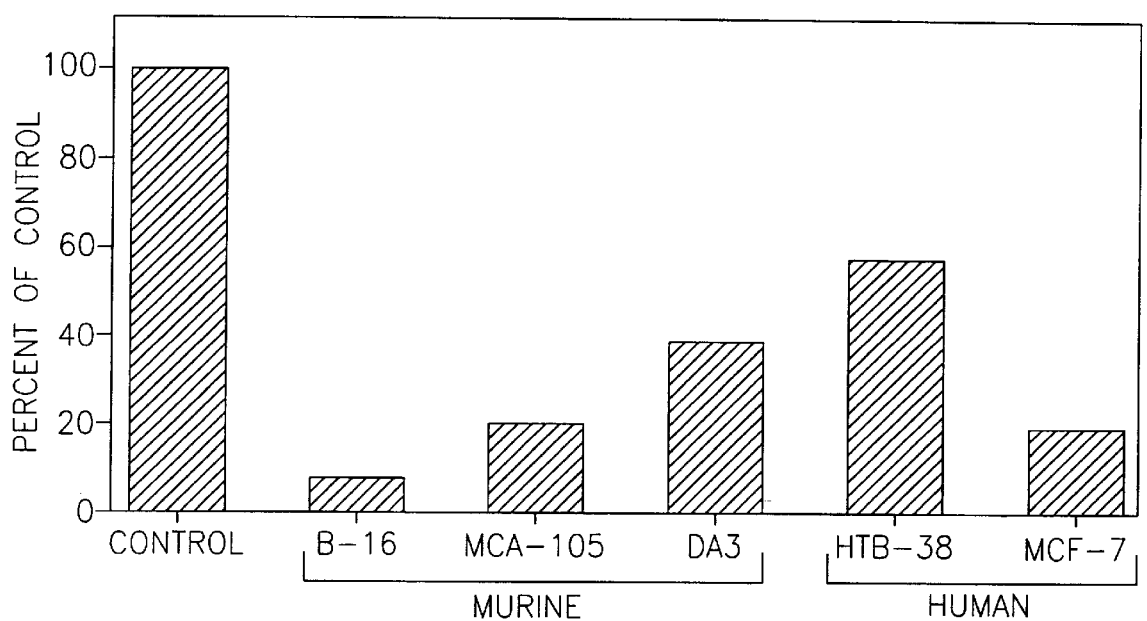

The effect of a 3,000 Dalton MF ultrafiltrate (non-diluted) derived from L-8 cells is also shown in FIG. 6 (results are shown as percent of control; the control in each experiment was rated 100%). As can in seen, the MF is active in inhibiting proliferation of all tested tumor cell lines.

Figure 7:
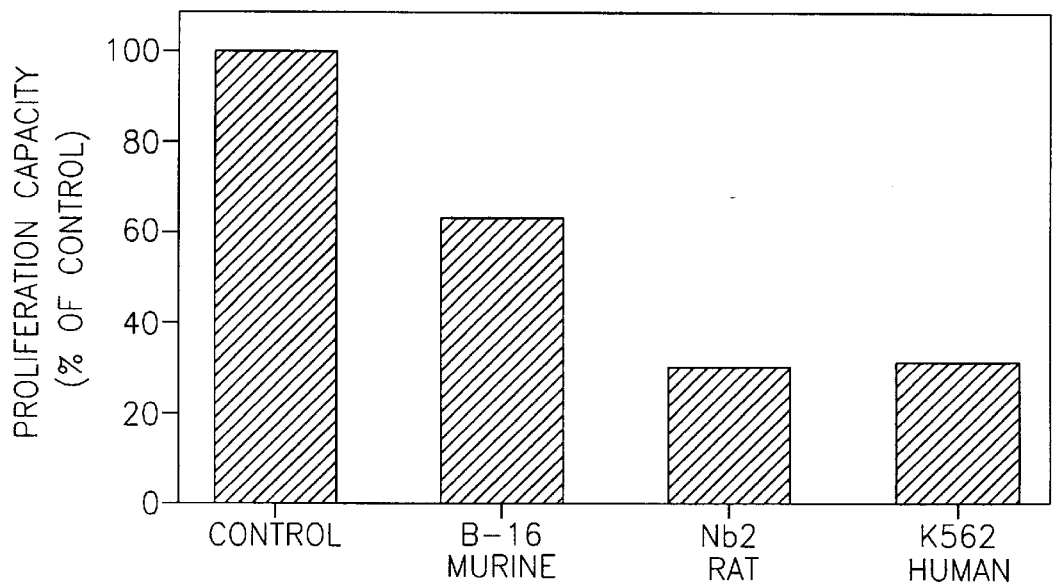

FIG. 7 shows the activity of a 3,000 Dalton MF ultrafiltrate derived from human myoblasts, in inhibiting proliferation of 3 cell lines (results are shown as percent of control). The proliferation of the B-16 and the K562 cells lines was tested by determining $^3$H-thymidine incorporation; the proliferation of the $Nb_2$ cell line was tested by means of cell count. It can be seen that the human-derived MF is active in inhibiting proliferation of all tested tumor cell lines.

Figure 15:
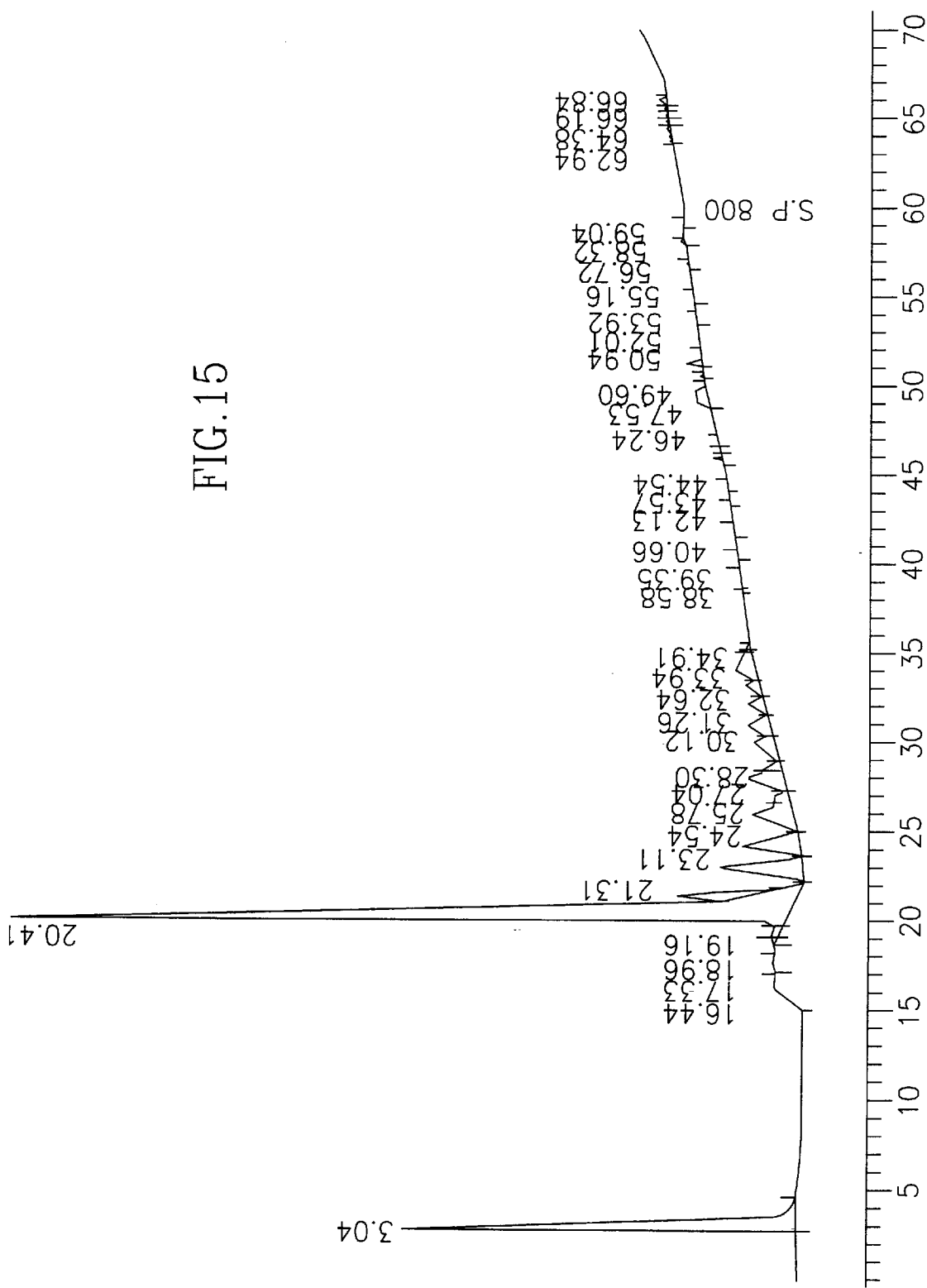
FIG. 15 shows a 220 nm elution profile of an MF-containing solution rechromatographed through an RP-HPLC column (the rechromatography was performed in the same way using the same column as the first chromatography).

In another experiment, fractions from a preparative RP-HPLC, which were found to be active in inhibiting proliferation of tumor cells (fractions 5 and 6 from FIG. 15), were pooled together, evaporated at 45° C. and then dissolved in 5 ml water, transferred into tubes and again dried in vacuum, and finally dissolved in 2 ml water and sterilized. Amounts of these fractions were tested to determine their ability to inhibit proliferation of three different cell flues: $Nb_2$-11C, $nb_2$-SP and IM-9, The results are shown in the following Table I (proliferation determined by cell count.

TABLE I

| Cell | Amount (ml/ml) | % Inhibition |
|---|---|---|
| $Nb_2$-11C | 0.05 | 49 |
| | 0.015 | 33 |
| | 0.005 | 22 |
| $Nb_2$-SP | 0.05 | 46 |
| | 0.015 | 26 |

TABLE I-continued

| Cell | Amount (ml/ml) | % Inhibition |
|---|---|---|
|      | 0.005 | 18 |
| IM-9 | 0.05  | 1  |
|      | 0.015 | 1  |
|      | 0.005 | 7  |

As can be seen, the MF inhibits proliferation of the hormone dependent $Nb_2$-11C tumor cell line as well as the hormone independent $Nb_2$-SP tumor cell line. Against this, the MF had essentially no effect on the non-tumorous, human lymphocyte cell line IM-9.

Figure 8:
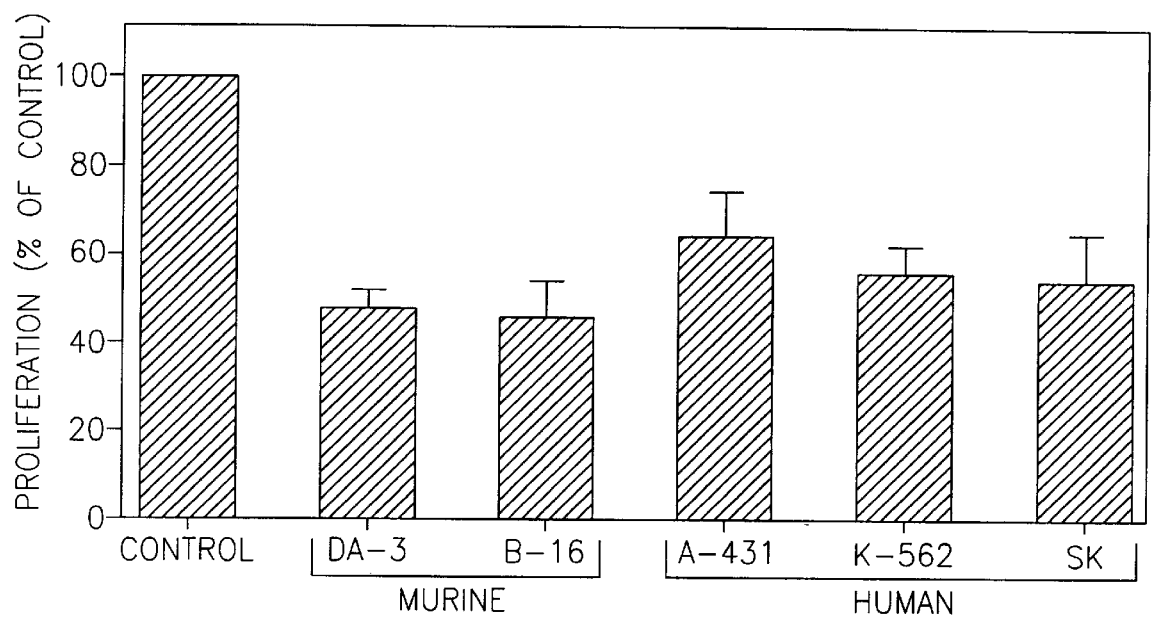

FIG. 8 shows the effect of a 3,000 Dalton WBF ultrafiltrate on the proliferation of murine an human cell lines. As can be seen here again, the WBF inhibited proliferation of all tested tumor cell lines of both murine and human origin.

4. In vitro inhibition of lymphocyte response to a PHA and of MLR by the MF and the WBF When lymphocytes from two individuals are cultured together, the HLA antigens of each individual will cause a cell reaction that will result in lymphocyte proliferation (the proliferation is directly related to the difference between the HLA antigens of the two individuals). To explore the effect of WBF or MF on this reaction, $1 \times 10^6$ cells/ml of mononuclear cells from two donors (the cells prepared as described above under 12), were incubated in PBS containing 10% FCS and different dilutions of a 3,000 Dalton MF or WBF ultrafiltrate was added to the cells. The cultures were incubated for five days at 37° C. in a humidified atmosphere of 5% $CO_2$, 95% air. During the last 6 hours of incubation, each well was pulsed with 1 $\mu$Ci $^3$H-thymidine. The cells were harvested and the H-thymidine uptake was determined in a LKB liquids scintillation counter (LKB, Piscataway, N.J., U.S.A.).

PHA (phyto hema agglutinin) is a mitogen which binds to the cell's surface sugars of lymphocytes and induces lymphocyte transformation to a blast form with a subsequent cell proliferation. To explore the effect of the MF or WBE on the PHA induced reaction, mononuclear cells, at a concentration of $10^6$ cells/ml were seeded into a 96 well microwell plates containing each 0.2 ml of RPMI supplemented with 10% fetal calf serum (Israel Industries, Bet-ha-Emek, Israel) and 1 $\mu$g/ml PHA (Wellcome Laboratories, U.K.). In some wells the 0.2 mil RPMI consisted of half native RPMI and half 3,000 Dalton MF ultrafiltrate from L-8 cells in RPMI. The cultures were incubated for four days in a $CO_2$ incubator and at the end of the incubation period the cells were pulsed with 1 $\mu$Ci $^3$[H]-thymidine, incubated for an addition 24 hours, and harvested with Dyatech cell harvester and the radioactivity was counted with an LKB scintillator.

Figure 9:
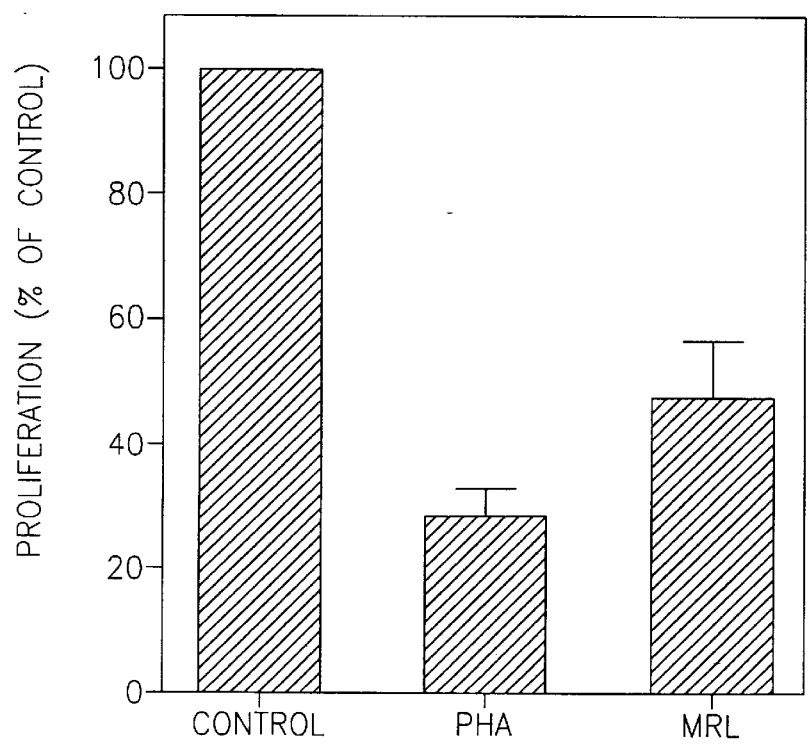

FIG. 9 shows the effect of the MF in inhibiting the lymphocyte reaction to PHA and on the MLR (the results that are shown for a 1:1 dilution, and are given as percent of control). Qualitatively similar results were obtained with WBF. Furthermore, the effect of both the MF and the WBF was proportional to the dilution (decrease of effect with increasing dilutions)(results not shown).

5. In Vivo Studies 5.1 Induction of tumor (MCA 105) by i.p. inoculation; i.p. treatment with MF:

30 C57BL6/J mice were injected intra peritoneal (i.p.) with $2.5 \times 10^5$ MCA-105 cells. The mice were treated twice daily by i.p. injections of 0.5 ml of the RP-HPLC fraction designated below (clause 6.5.2) as MF-SP. The mice were sacrificed on day 33, and the tumor foci were evaluated.

Figure 10:
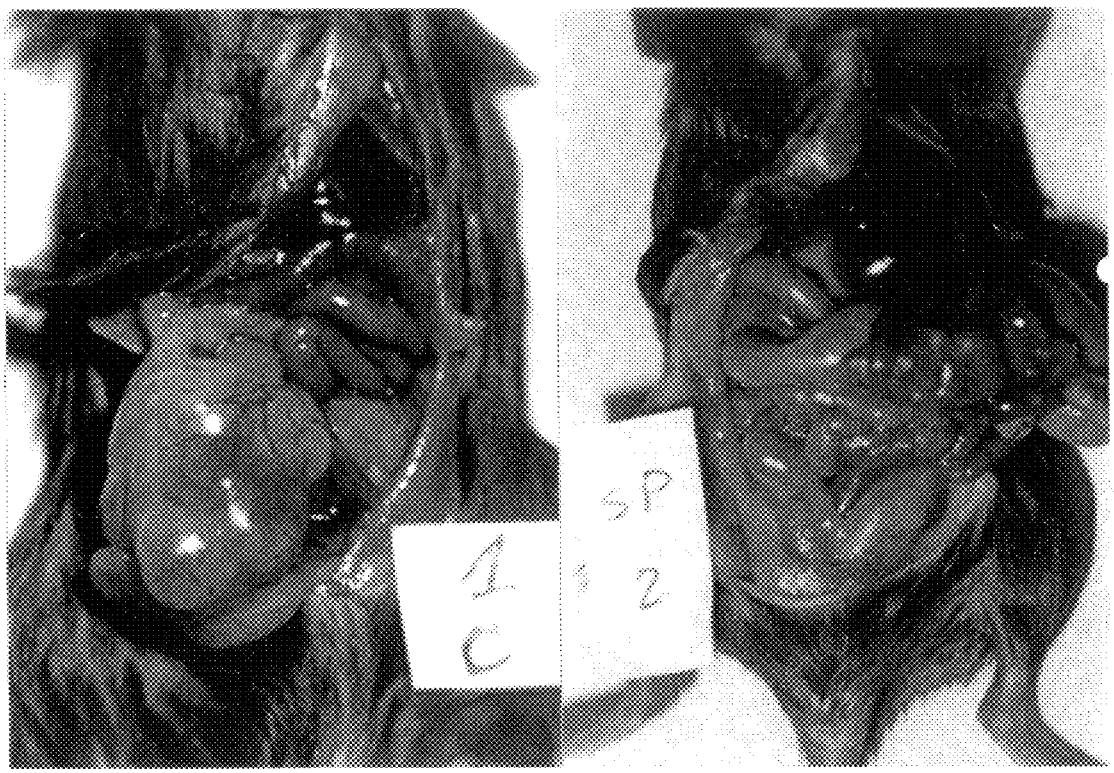
FIG. 10 is a picture showing the exposed peritoneum of two representative mice, in which a tumor was induced by an intra peritoneal injection of $2\times10^5$ MCA-105 cells. Following injection, the mouse on the right was treated twice daily by an intra peritoneal injection of 0.5 ml of an MF containing fraction eluted from a preparative reverse phase (RP) CIS high pressure liquid chromatography (HPLC) column (this fraction is referred to as "MP-SP" in the text below (see 7.6.2)); the mouse on the left was injected with a control RPMI medium.

Representative results are depicted in FIG. 10, showing two animals, with an open peritoneum, wherein the animal shown in the left panel was treated with the MF-SP fraction and the animal shown in the right panel was treated with a control RPMI medium. As can be seen, a very large tumor growth is observed in the control animal whereas, only very small, hardly noticeable, tumor foci were observed in the MF-treated animal.

Figure 11:
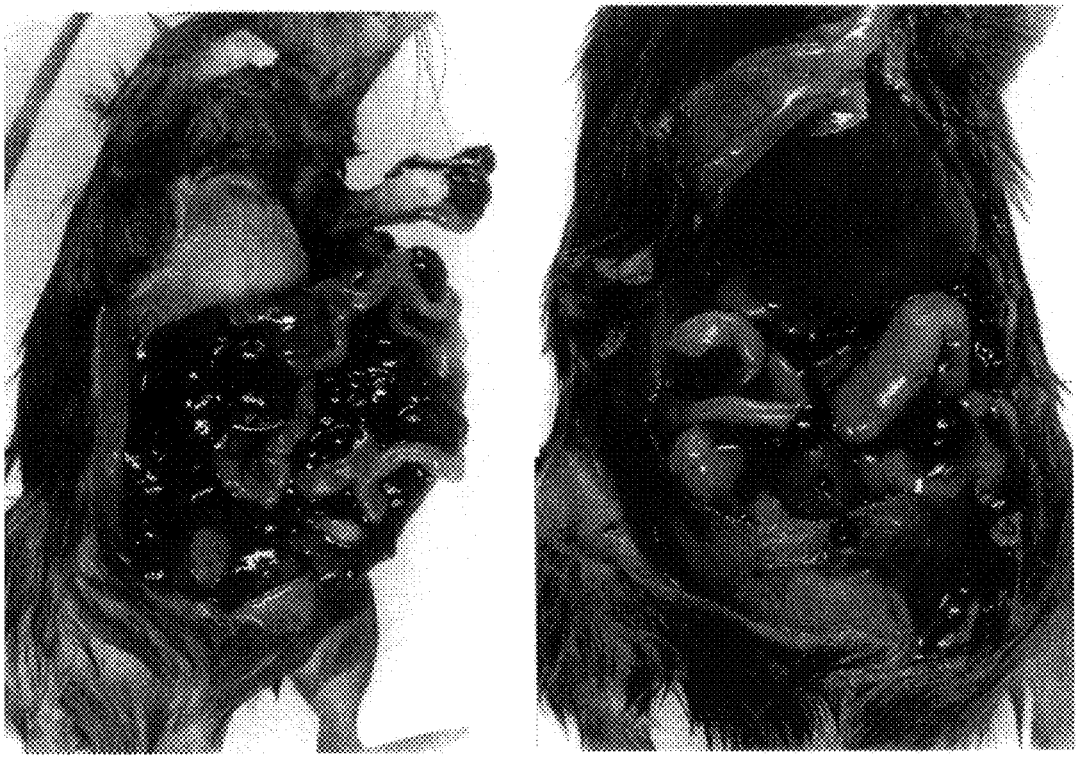
FIG. 11 is a picture showing the exposed peritoneum of two representative mice in which a tumor was induced by intra peritoneal injection of $5\times10^5$ B-16 melanoma cells. The picture on the right is of a mouse treated once daily with an i.p. injection of 1 ml 3,000 Daltons MF ultrafiltrate (in PBS) derived from the L-8 cells the picture on the left is of a arouse treated once daily with a control PBS medium, injected i.p.

5.2 Induction of a tumor (B-16 melanoma) by i.p. inoculation; treatment by i.p. injection of MF 40 C57BL6/J mice were injected i.p. with $5 \times 10^5$ B-16 melanoma cells. 20 mice served as control and were injected daily, i.p, with a PBS solution. 20 mice were treated daily with 1 ml of 3,000 Dalton MF ultrafiltrate derived from L-8 cells. The mice were sacrificed on day 15 and the extent of tumor growth on the peritoneum of the animals was tested. It be seen in FIG. 11, which depicts open peritonea of two representative mice from each experimental group, that while large numerous tumor foci can be seen in the animal from the control group, there are only a few and such smaller tumor foci in the treated animal.

5.3 Induction of a tumor (MCA-105) by i.p. inoculation; treatment with MF by both i.p. and pro. administration 30 C57BL6/J mice were injected i.p. with $2.5 \times 10^5$ MCA-105 cells. 10 mice were treated daily by per ost (p.o.) administration of 1 ml of the 3,000 Dalton MF ultrafiltrate derived from the L-8 muscle cell); 10 mice were treated daily by i.p. injection of the same solution; and 10 mice served as control group and were treated daily, p.o. with an RPMI medium.

Figure 12A:
FIGS. 12A and 12B is a picture showing exposed peritonea of representative mice injected i.p. with $2.5\times10^5$ MCA-105 cells. The mice shown in FIG. 12A are from a group of mice which were treated daily (beginning at the day of tumor inoculation) per oz (p.o.) by 1 ml of a 3,000 Dalton MF ultrafiltrate derived from L-8 cells. The mice shown in FIG. 12B are from a control group of mice treated p.o. with a control RPMI medium.
Figure 12B:

The mice were sacrificed on day 30, their peritonea were exposed and tested for the extent of tumor growth therein. Two representative mice from each group are shown in FIG. 12 (FIG. 12A—MF treated mice; FIG. 12B—control), As can be seen in FIG. 12A, there are no signs of tumor growth in the peritonea of the MF-treated animals, while big tumor foci appear in the peritonea of the animals of the control group. In this experiment, 90% of the mice of the control group developed tumor foci, while foci developed in only 40% of the mice treated either i.p. or p.o. with the MF.

5.4 Induction of a tumor by i.m. inoculation (DA3 breast carcinoma); treatment with MF by imp. and p.o. administration $1 \times 10^6$ DA3 cells were injected intramuscularly (i.m.) to the leg of 30 BALB/C mice. 10 mice served as a control and were treated daily by i.p. injection of PBS; 10 mice were treated daily by i.p. injection of 1 ml of a 3,000 Dalton ME ultrafiltrate derived from the L-8 muscle cells (prepared in PBS); and 10 mice were treated with the same MF-containing solution by p.o. administration (1 ml). The mice developed big tumors in the leg and after three weeks, the mice were sacrificed and metastatic lung foci could be detected and counted in the lung. In the control group 23.4±6 metastatic foci were counted in comparison to 6.2±1.3 foci in the imp. treated group and 2.2±0.6 in the p.o. treated group.

Figure 13:
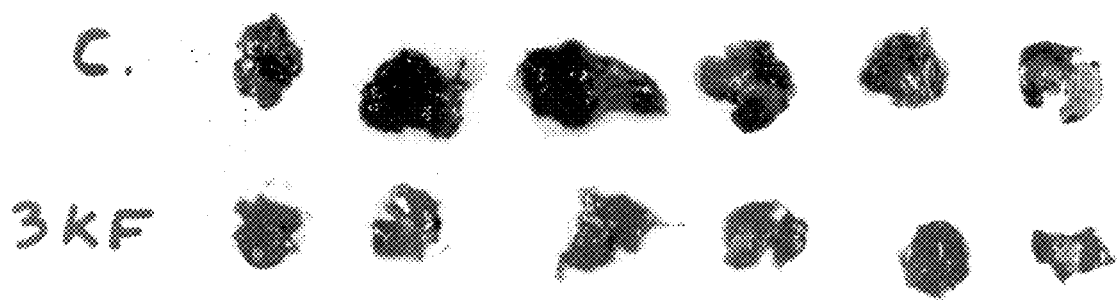
FIG. 13 is a picture showing isolated lungs of mice which were injected i.v. with $5\times10^5$ B-16 melanoma cells. The lungs in the upper row were from a control group of animals administered daily, p.o. with 1 ml of a control, PBS solution. The lungs in the low row were from the experimental group which consisted of animals treated daily by p.o. administration of 1 ml of a 3,000 Dalton MF filtrate obtained from the L-8 cells.

5.5 Induction of a tumor by i.v. inoculation (B-16 melanoma); treatment with MF by pro. administration 30 C57BL/6J mice were intravenously injected with $5 \times 10^5$ B-16 melanoma cells. 20 mice were treated by daily p.o. administration, beginning the day of tumor inoculation, with 1 ml of a 3,000 Dalton MF ultrafiltrate derived from L-8 cells; 10 mice served as control and were administered p.o. with PBS only. On day 18, the mice were sacrificed and developed black tumor foci could be observed in their lungs. Representative lungs of the two groups can be seen in FIG. 13 (upper row—control; lower row—MF treatment). As can be seen, while there are many black metastatic foci in the lungs of the control group, only a few and small can be seen in the experimental group.

6. Degree of WBF secreted from white blood cell from healthy individuals and cancer patients Mononuclear cells were isolated from venus blood of 23 healthy individuals (samples obtained from a blood bank) and from 33 hospitalized cancer patients. The procedure was as described under 1.2. Supernatants were collected from cultures of $2 \times 10^6$/ml mononuclear cells, the supernatant was collected and then ultrafiltrated through a filter having a molecular cutoff of 3,000 Daltons, as described under 2.

The ultrafiltrates were tested for its ability to inhibit growth of cancer cells from 3 cancer cell lines: B-16 murine melanoma, SK human melanoma, and K-562 human leukemia cell line.

Figure 14A:
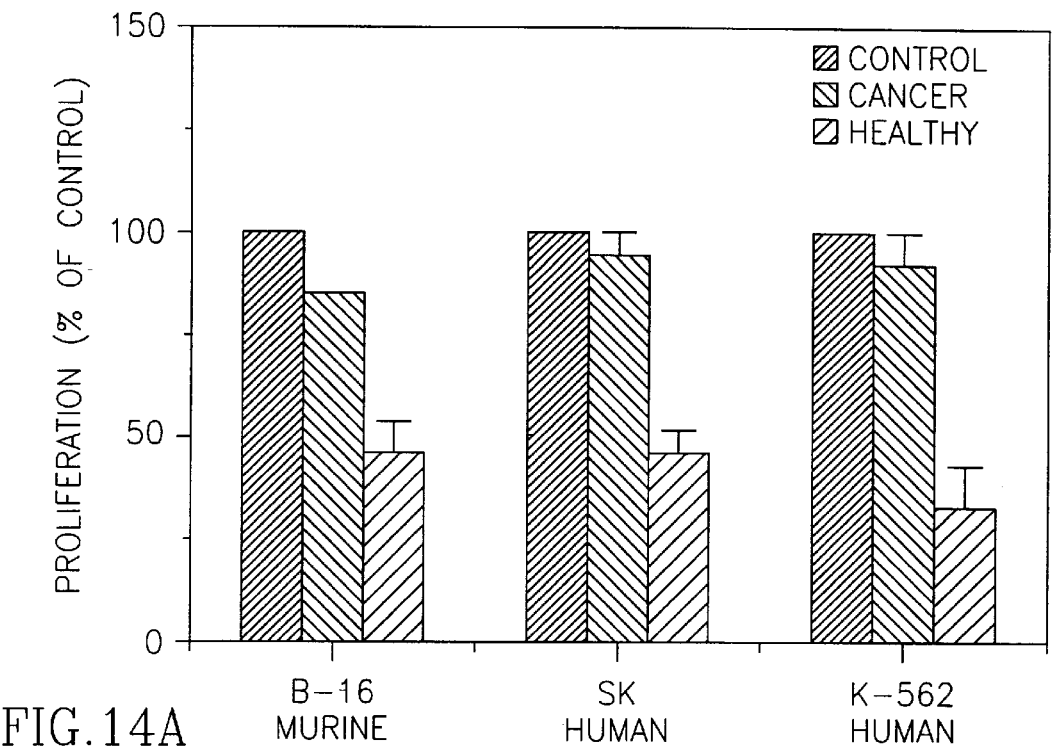
FIG. 14A and 14B show the effect of a 3,000 Dalton ultrafiltrate from the supernatant of white blood cells from blood of cancer patients and from blood of healthy individuals, in inhibiting proliferation of three tumor cell lines (B-16, SK and K-562)
Figure 14B:
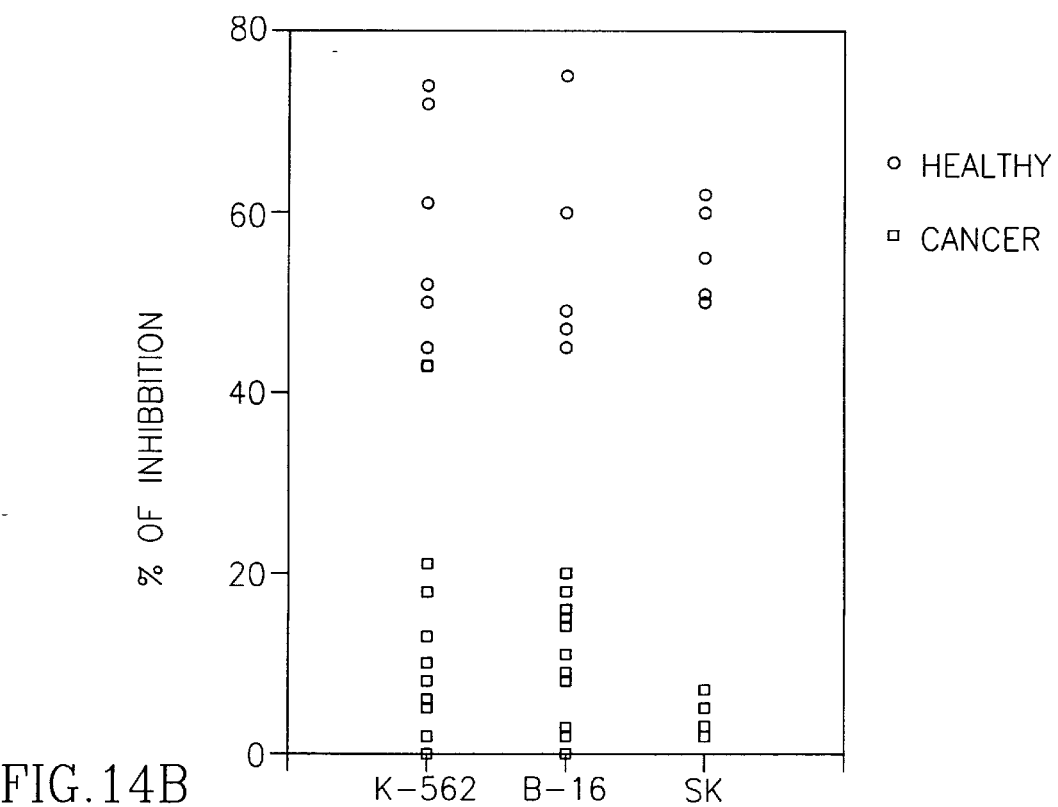

Results are shown in FIG. 14. As can be seen in FIG. 14A, while the ultrafiltrate from mononuclear cells of healthy individuals showed a marked inhibition of proliferation, which was below 50% of the cell lines tested, there was only a very little, hardly significant inhibition of proliferation with the ultrafiltrate from the cancer patients. As can further be seen in FIG. 14B, there is absolutely no overlap between the two groups.

These results show that there is a considerably lower degree in the level of WBF secreted by mononuclear cells from cancer patients, as compared to that secreted by lymphocytes from healthy individuals. These results thus demonstrate the diagnostic significance of testing the level of the LMW-EGR of the invention. In addition, the power level of WBF has also an important therapeutic significance.

7. Characterization of MF 7.1 Bioassay

The muscle cell CM was fractionated, as will be detailed further below, and the various fractions were assayed using the above-mentioned cell lines. The effect of each fraction on the cells growth was determined by the $^3$H-Thymidine uptake or by the cell count assays described above.

7.2 Testing for a putative protein nature of MF

In order to determine whether MF is a proteinaceous substance or not, the muscle cell CM (derived from a primary rat muscle cell culture) was subjected to a series of treatments including sensitivity to proteolytic enzymes, stability during lyophilization, and effect of incubation at various temperatures. Following such treatments, the CM was brought back to the original salt and protein concentration by dilution with the original medium, or if diluted, the dilution factor of the protein concentration was taken into account in evaluating the results. The assay which was used was the $^3$H-thymidine uptake assay.

7.2.1. Effect of proteolytic enzymes

Trypsin and pronase, two proteolytic enzyme preparations, were tested. In order to determine the effect of trypsin, two procedures were used:

(i) MF-containing solution was incubated with trypsin (0.5–2 μg/ml) for 4 hours at 37° C., following which the trypsin activity was stopped by the addition of an approximately 2-fold molar access of soybean trypsin inhibitor (STI). A non-conditioned (MF-free) medium was used as control:

(ii) MF-containing solution was incubated with trypsin (0.5–2 μg/ml) for 1–4 hours at 37° C., or overnight at room temperature, and following the incubation the enzyme was removed on a column of P-aminobenzamidine-agarose. An MF-free medium served as control. Further control tests with trypsin alone have shown that no tryptic activity is eluted from this column under the running conditions of the column bicarbonate buffer.

In order to test the effect of pronase, the muscle cell CM was treated by bringing it into contact with pronase immobilized on a sepharose gel. Also here, an MF-free medium was used as control. The results are shown in the following Table II (the number indicates % inhibition as compared to a non-conditioned control medium).

TABLE II

| Experiment Cell Type | Trypsin + STI[a] | | Trypsin + column[b] | | Pronase-Sepharose | |
|---|---|---|---|---|---|---|
| | Untreated | Treated | Untreated | Treated | Untreated | Treated |
| HTB 38 | 35 | 30 | 40 | 40 | 53 | 75 |
| MCA | —[c] | — | 25 | 27 | 62 | 70 |

[a]Trypsin procedure (i) above
[b]Trypsin procedure (ii) above
[c]"—" = not tested The above demonstrate that treatment with trypsin by both procedures as well as with pronase, had no significant effect on the tumor growth inhibitory activity of MF.

7.2.2. Lyophilization

A muscle cell CM was lyophilized without prior dialysis and the lyophilizate was then redissolved in water to its original volume. Following this treatment there was no appreciable loss in the MF's activity of inhibitory tumor growth, thus indicating that MF is stable to lyophilization 7.2.3. Heat treatment A muscle cell CM (derived from a previous rat muscle cell culture) was treated for various periods of times at temperatures in the range of 4–100° C. Following those treatments the samples were tested with both MCA and cells. The results are shown in the following Table III (the numbers indicate change (in %) in inhibitory potency of MF following the temperature treatment):

TABLE III

| Temp., ° C. Time | 4 | 22 | 40 | 60 | 100 |
|---|---|---|---|---|---|
| 1 min. | — | — | — | +13 | — |
| 5 min. | — | — | — | — | +26 |
| 1 hour | — | — | +16 | +29 | +6 |
| 22 hours | +61 | +42 | — | — | — |

"—" = not tested under such conditions

In other sets of experiments, a 3,000 Dalton ultrafiltrate of the conditioned medium was treated by heating to boiling, without any loss of the activity of this low molecular weight fraction in inhibiting proliferation of tumor cells.

The above results show that there was no decrease in inhibitory potency under all the tested temperatures, including boiling at 100° C.

7.2.4 Summary

No decrease in the potency of MF to inhibit growth of tumor cells was observed under the conditions tested, which clearly point to that the MF is not a protein Against this, the results showed an increase in inhibitory activity following some treatments which may be explained by the fact that the MF-containing medium contains a proteinaceous factor which exerts an opposite effect to MF and which is destroyed in the treatment.

7.3 Size of MF

MF-containing CM has been fractionated by ultrafiltration on Amicon membranes with molecular cut-offs of 10, 2 and 0.5 kD (the retentate was difiltered in a each case with at least one additional PBS volume). in the cases of both the 10 and 2 kD membranes, essentially all the inhibitory activity (above 90%) was found in the first two filtrates, and with the 0.5 kD membrane, approximately 80% of the activity was found in the filtrates and some activity (20%) was retained in the second retentate. the inhibitory activity was assayed in each case on both HTB 38 and MCA cells.

Dialysis of the MF containing CM through membranes with molecular cut-offs of 12 and 3kD, showed that the active component escaped through both membranes.

The above results show that the ME has a molecular weight in the order of or less than about 500 Daltons or less.

7.4 RP-HPLC characterization of MF (derived from a primary culture of rat muscle cells)

Filtrates of the 10 kD membranes were chromatographed on a C-18 reverse phase (RP) column (4×250 mm). The filtrate was brought to the original concentration by dilution in a solution of 0.1% trifluroacetic acid (TFA) before being applied to the column, which was developed with a 5–35% gradient of acetonitrile (both these components were tested previously to determine that they did not effect inhibitory activity of MF). The activity which was tested with HTB-38 cells, eluted at 15% acetonitrile in 0.1% TFA. The active fraction was then rechromatographed on the same column in the acetonitrile gradient and a partially purified MF elated at the same position as before (retention time about 21 mins.). A third run of RP chromatography was performed on this last fraction under the same conditions as the first two runs. A single inhibitory peak was found, and it coincided with the position of a 220 nm absorbance peak in the elution profile which can be seen in FIG. 15.

7.5 Large scale purification of MF (derived from a primary culture of rat muscle cells)

7.5.1. Experimental protocol

Rat muscle cell CM was ultrafiltered on Amicon 10 kD membranes. The 10 kD filtrate was chromatographed on a C-18 reverse phase (RP) column (47×300 mm) attached to a preparative HPLC column. Fractions were tested in a cell proliferation assay using HTB-38 cells, and the active fraction was rechromatographed on a second C18 RP column (analytical: 4×250 mm) and the active fraction was identified as above.

7.5.2. Activity of purified MF fractions

The material obtained in the last step in Section 7.5.1. was termed "MW-P" whereas the material obtained after the first RP column was termed "MF-SP" (this fraction is also the one tested in Section 5.1). The activities of the crude condition medium (CM), the MF-P and MF-SP fraction as well as the retentate (R) of the ultrafiltration, is shown in the following Table IV (activity is expressed in u/ml: 1u is defined as the amount of material causing 50% inhibition in the proliferation assay):

TABLE IV

| Cell line | CM | "MF-P" | "MF-SP" | "R" |
|---|---|---|---|---|
| HTB-38[a] | 18.0 | 8.4 | 21.6 | — |
| HTB-38[a] | — | — | 30.0 | 10.2 |
| MCA | — | 7.4 | 8.4 | 5.0 |

[a] = Experiments with HTB-38 cells were performed separately in two different locations.
"—" = not tested As can be seen all fractions tested were active in inhibiting proliferation of the tested cell lines. This included also the R fraction, the factor active there being possibly the tumor proliferation inhibitory agent disclosed in U.S. Pat. No. 5,242,692.

7.6 Characterization by HPLC of MF derived from the L-8 cell line

In Sections 7.6.1–7.6.5 some representative HPLC results are demonstrated. In Section 7.6.1, an exemplary method for the purification of the MF is given.

7.6.1. Reverse Phase (RP)HPLC 160 ml of a 3,000 Dalton MF ultrafiltrate, in PBS (obtained after 8 hrs incubation of the muscle cells with the PBS) were chromatographed through an RP-HPLC column (C18). The elution fluid was a gradient of HPLC grade water prepared in a B-pure™ (Barnstead, Dubuque, Iowa) device, and HPLC grade acetonitrile (G. T. Baker, U.S.A.). The elution fluid gradient was between 0% acetonitrile to 60% acetonitrile over a 30 min. period. The flow rate was 100 ml/min. Two minute fractions (each consisting of 200 ml) were collected.

20 ml of each of the obtained HPLC fraction were evaporated until dryness in a concentrating centrifuge, and the dried fractions were then suspended in 100 μl of water, then evaporated again until dryness, then dissolved in 2 ml PBS, and the fractions were then tested for their proliferation inhibitory activity in the cell count assay, by applying 0.2 ml from each fraction into a tester cell-containing microwell.

Figure 16:
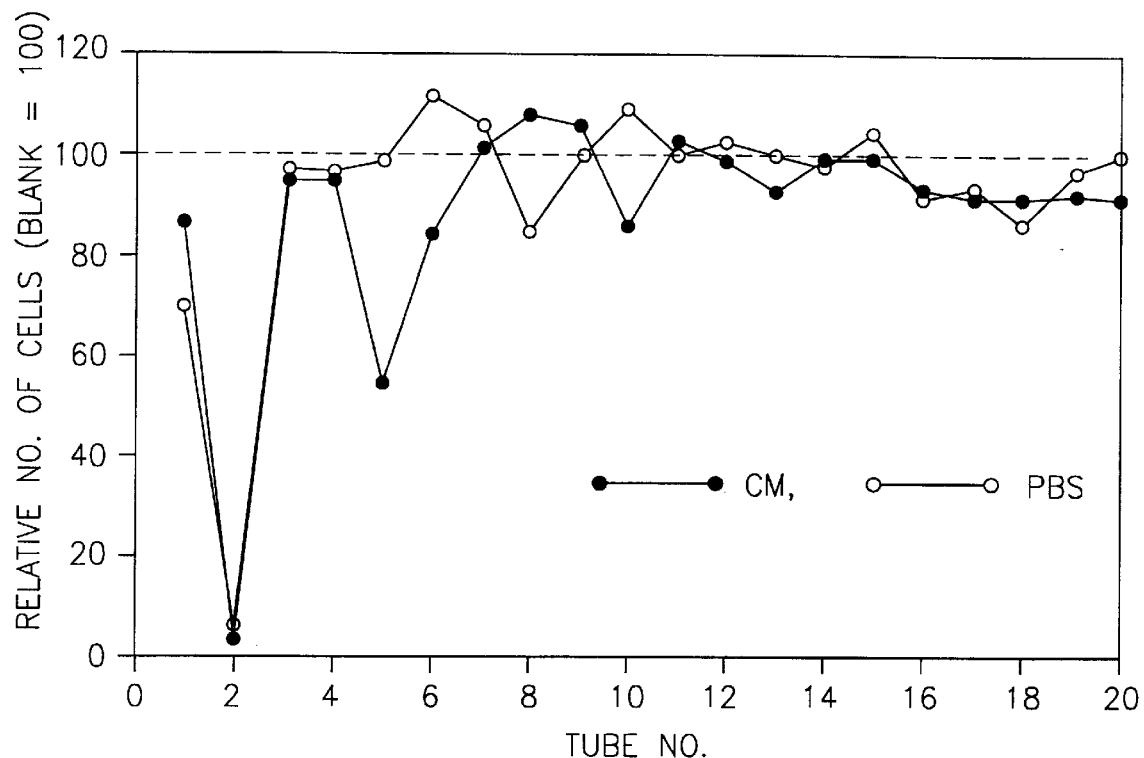
FIGS. 16–21 show the activity of various fractions eluted from various HPLC columns in inhibiting proliferation of $Nb_2$ cells, determined by cell count. The abscissa in each of these pictures shows the tube number (regarding the rate of flow and the volume of each tube, see below in the text). The ordinant shows the relative number of cells as compared to a blank (cells grown without addition of any solution to the growth medium of the $Nb_2$ cells, being 100%).
Figure 17:
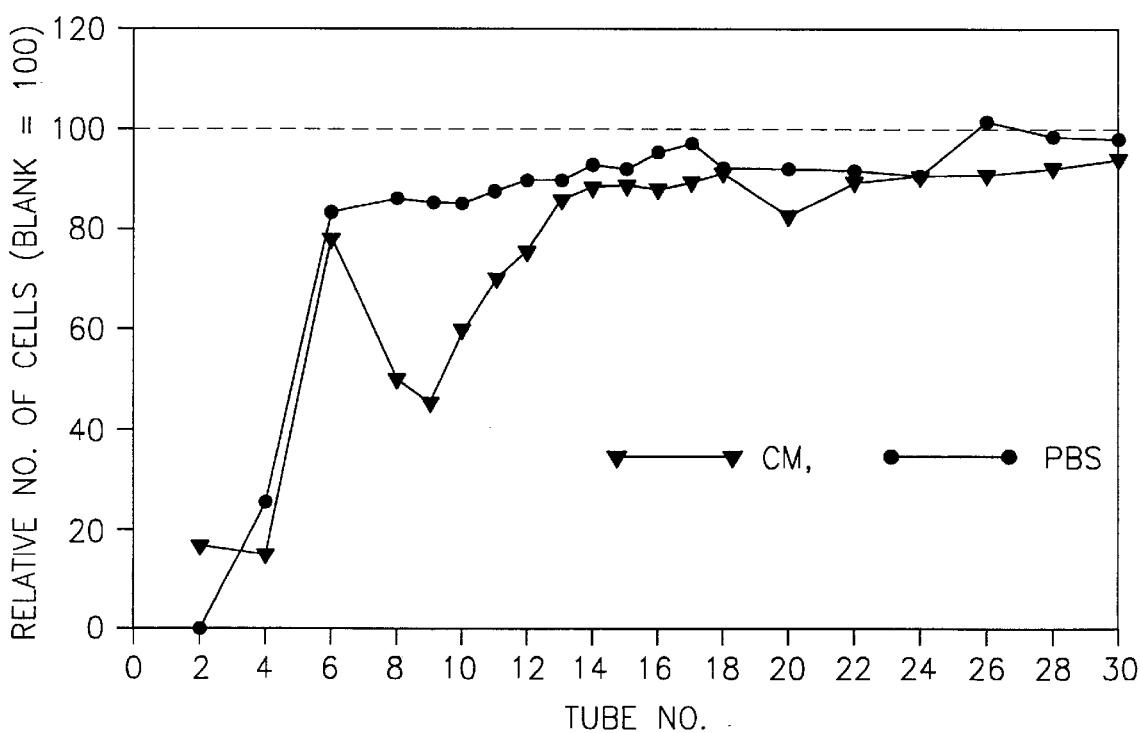

FIGS. 16 and 17 show the activity of various fractions in two different runs. Results of both cases show the presence of a specific inhibition, which eluted in Fractions 5 and 6 in FIG. 16, and in Fractions 8–12 in FIG. 17.

Fractions 5 and 6 from FIG. 16 were pooled, evaporated at 45° C. dissolved in 5 ml water, transferred into tubes and again dried in vacuum, dissolved in 2 ml water and sterilized. 1 ml of these concentrated fractions were chromatographed in an analytical RP-HPLC (C-18) column in a gradient of running fluids between 100% water and 60% acetonitrile within 20 minutes, the flow rate being 1 ml/min. 1 minute fraction (each of 1 ml) were collected, then dried, dissolved in 0.4 ml RPMI containing 5% HS and sterilized. 0.15 ml were added into each cell-containing well (the activity was determined by the cell count assay). For control, PBS solutions was fractionated by HPLC and tested for activity in a similar manner.

Figure 18:
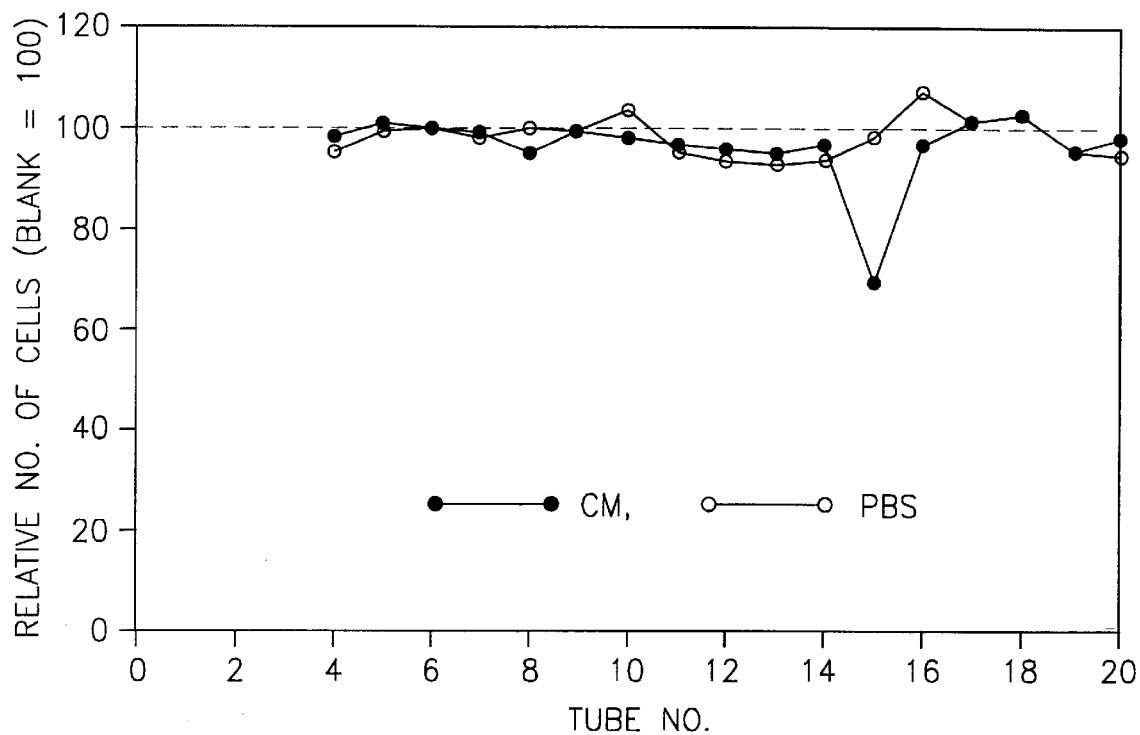

The activity of the various eluted fractions is shown in FIG. 18. These results indicate presence of a specific inhibition in fraction 15.

7.6.2 HPLC with a Superdex column

The active fractions of FIG. 17 were divided into two pooled fractions; a first fraction termed "FR1" was obtained from the combination of 1200 ml from tubes 6–8, 550 ml from tubes 8–9, 300 ml from tubes 9–10 and 30 ml from tubes 10–11; a second fraction termed "FR2" was obtained from 250 ml of tubes 9–10, 520 ml of tubes 9–11, and 600 ml of tubes 11–12. Each of FR1 and FR2 were dried and dissolved in 10 ml distilled water. Since an insoluble precipitate was formed after centrifugation, these fractions were further extracted with 10 ml (in the case of FR1) and 5 ml (in the case of FR2) of PBS. Even after the second extraction a considerable precipitate remained.

The results showed that most of the activity was present in FR1; FR2 had only about 15–20% of the activity of FR1. PBS extract of the insoluble preparation yielded only about 4% of the activity as compared to FR1.

2 ml of FR2 were dried and dissolved in 0.4 ml water. 0.2 ml were applied to superdex column equilibrated with PBS. The column was developed at 1 ml/min, with PBS as the running fluid and 1 ml fractions were collected. The collection started 0.3 min. after start of the separation. The eluted fractions were sterilized and 0.2 ml were added into each well.

Figure 19:
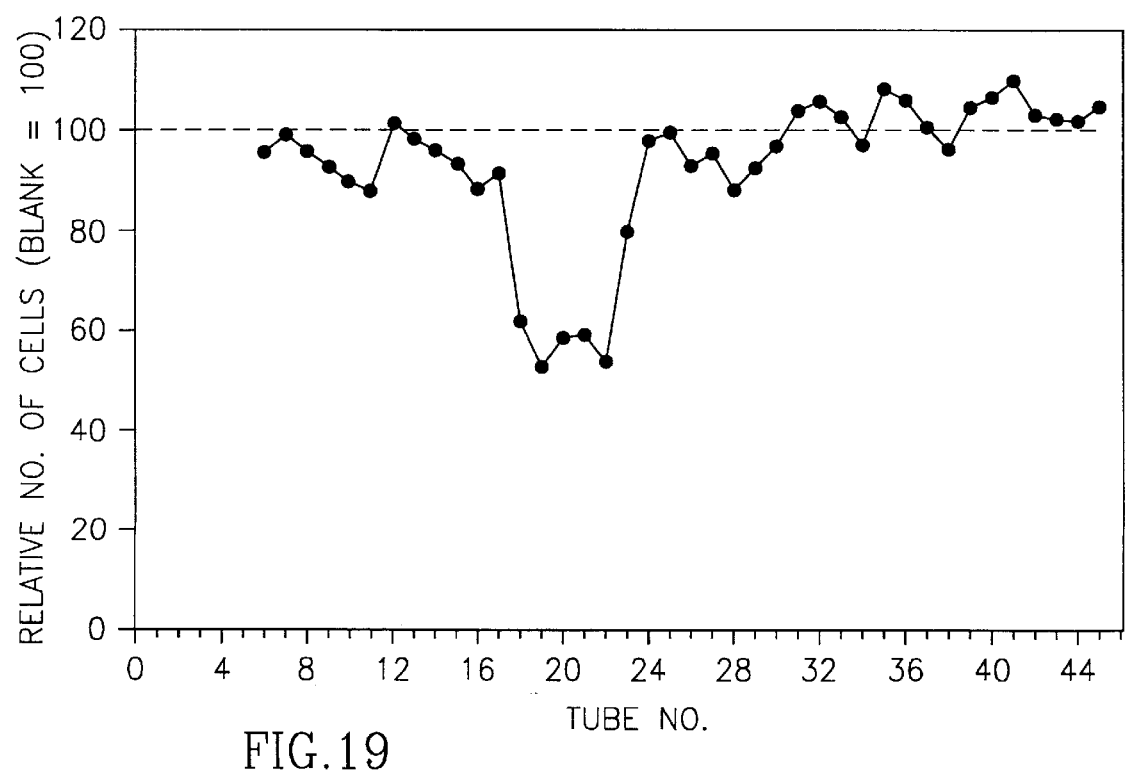

The inhibition of the various fractions eluted from the superdex column as shown in FIG. 19. A specific inhibition can be seen in fraction 18–22. Fractions 18–22 were pulled and rechromatographed on the same column under the same conditions. The rechromatography results indicate a possibility that there is a mixture of two or more active agents ("MF's") in these fractions.

A similar elution profile, was also obtained with FR1, although the results seems to indicate that FR1 was about 10 times more concentrated in its MF content as compared to FR2.

7.6.3 Analytical RP-HPLC following Superdex HPLC

Figure 20:
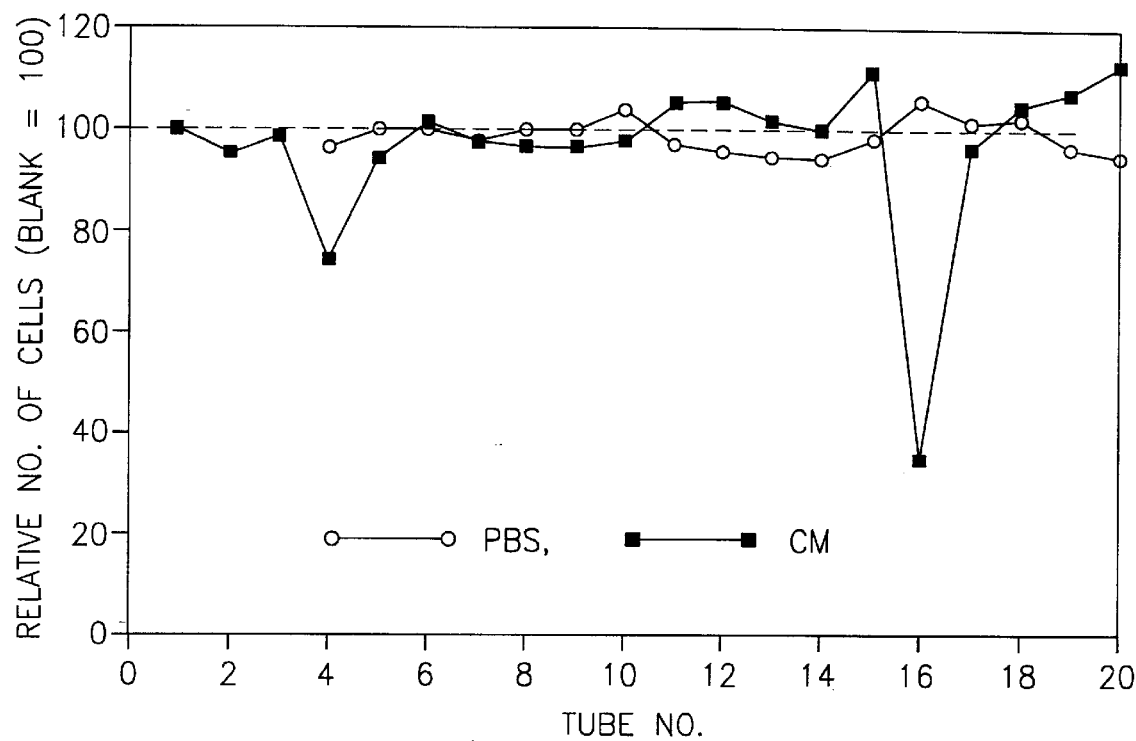

Fractions FR1 and FR2 were pooled and 1 ml aliquots were applied to an anlytical RP-HPLC (C-18) column. 1 ml fractions were collected, dried and dissolved in 0.4 ml RPMI containing 5% HS and 0.5 ml of this solution was added to each cell-containing well. Results are shown in FIG. 20. As can be seen, there is one sharp peak of activity in tube 16. In addition, there was also a low inhibitory activity in tube 4. These results indicate that there may be more than one tumor proliferation inhibiting agent in the muscle cell CM.

7.6.4 Size exclusion (SE) HPLC

Fractions 6–8 ("A"), 8–10 ("B"), 10–12 ("C") and 12–14 ("D") from the preparative RP-HPLC were separately chromatographed on a column containing silicone gel particles coated with polyhydroxyethyl aspartamide (PolyHYDROXYETHYL-A™, manufactured by PolyLC). The running fluid was an isocratic solution (i.e. with no gradient) which was an aqueous solution of 50 µM formic acid.

Figure 21:
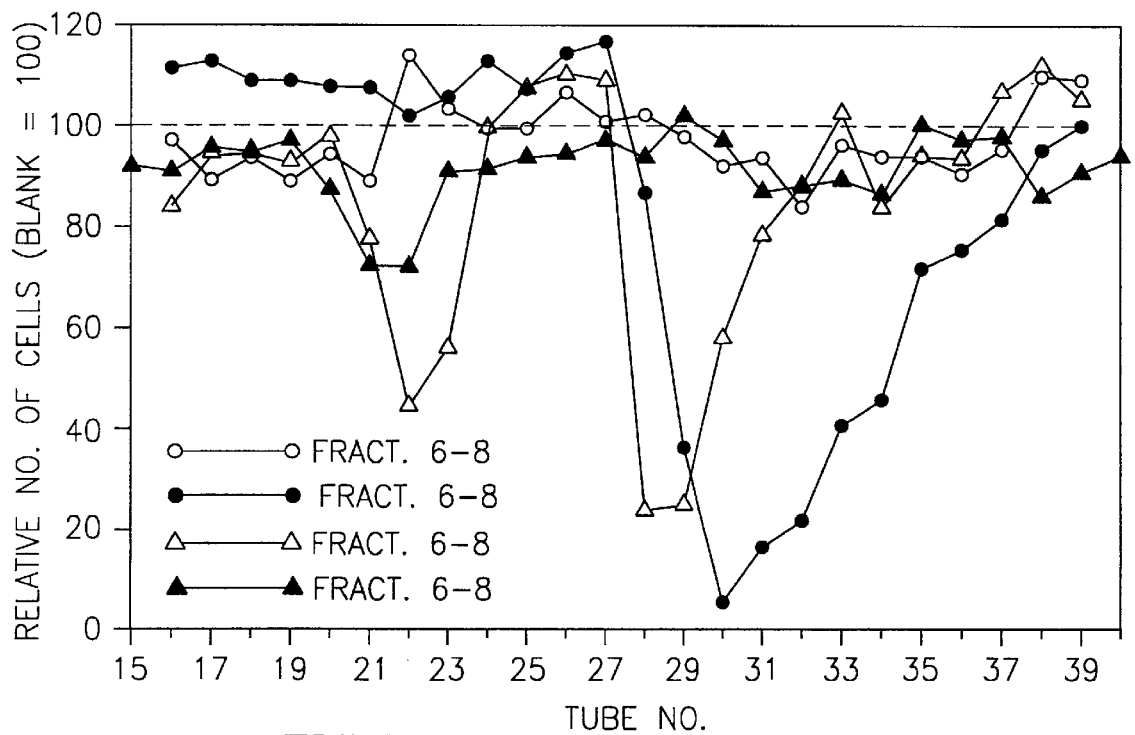

Fractions of 0.5 ml were collected, dried and dissolved in 0.8 ml PBS. 0.15 ml of each fraction were then added to each cell-containing well. The chromatography results can be seen in FIG. 21. The results show that there was no activity in Fraction 6–8, except perhaps a weak activity in tube 32. In Fraction B very clear and broad peak of activity can be seen in tubes 29–37. In Fractions C there are two clear peaks of activity, one in tubes 21–23 and the other in tubes 28–31. Finally, in Fraction D there appears to be a single peak of activity in tubes 21–22.

7.6.5 Superdex HPLC following SE-HPLC

Active fractions eluted from the SE column, were pooled and dried in a concentrating centrifuge under high vacuum (Hetovac™ VR-1, manufactured by Heto, Denmark), dissolved in 0.4 ml, and then 0.2 samples were separated on superdex columns, equilibrated with PBS. Fractions of 1 ml were collected, and 0.2 ml were then added to each cell-containing ell.

Figure 22A:
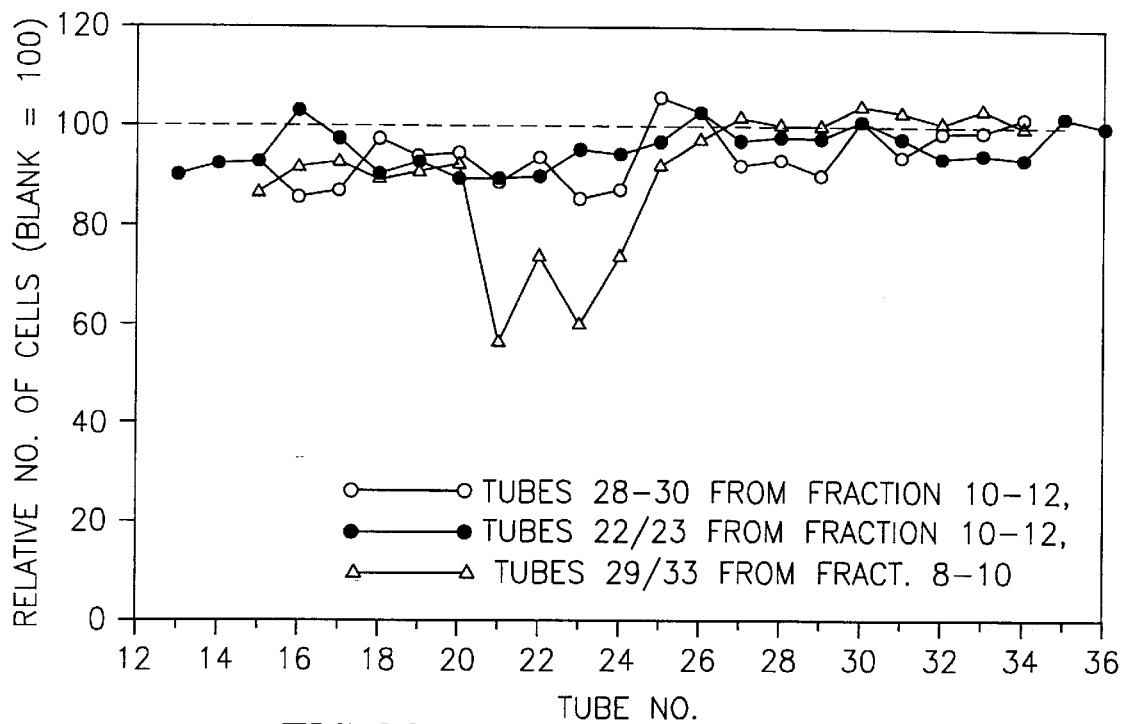
FIGS. 22A and 22B show the activity of various fractions eluted from a superdex column, in inhibiting proliferation of $Nb_2$ cells. The solutions fed into the column consisted of various fractions from the eluate of FIG. 21, as follows.

As can be seen in FIG. 22A, SE-HPLC tubes 29–33 of Fraction B showed inhibitory activity in tubes 21–24 eluted from the superdex column. The profile of this activity may indicate the possibility that there is more than one active agent, or that the active agent appears in several forms.

Figure 22B:
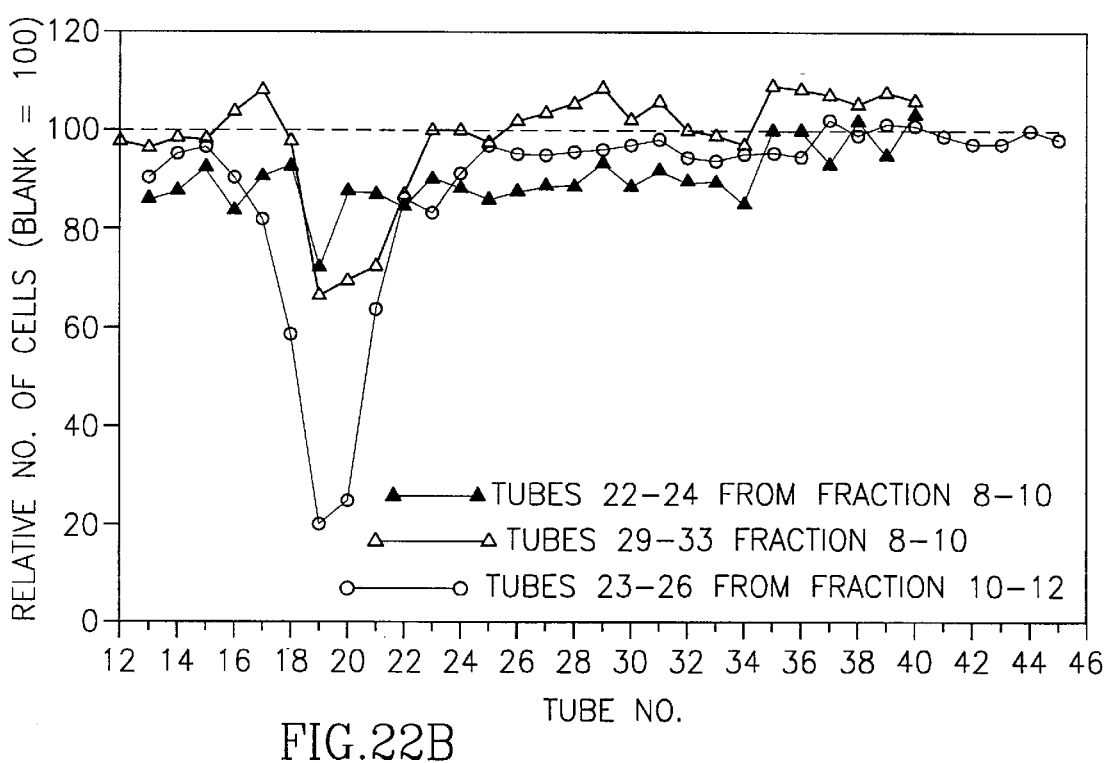

FIG. 22B shows a specific inhibitory peak eluted at 17–21 mins.

7.6.6 Hydrophilic interaction HPLC:

Fractions 27–32 from the aliquot of a size exclusion HPLC shown in FIG. 25 below, were pooled together, dried and dissolved in 0.2 ml water, Two amounts each of 0.085 ml were injected into a hydrophilic interaction (CHO) HPLC column (PolyGLYCOPLEX™, manufactured by Poly-LC). The column was then developed with a solution consisting of 70% acetonitrile in water at a running rate of 1 ml/min. 1 ml fractions were collected, dried and dissolved in 0.6 ml PBS and then 0.1 ml fractions were added into each well of a 96 microtiter plate and tested in the saline count assay (Section 3.1.3).

Figure 23:
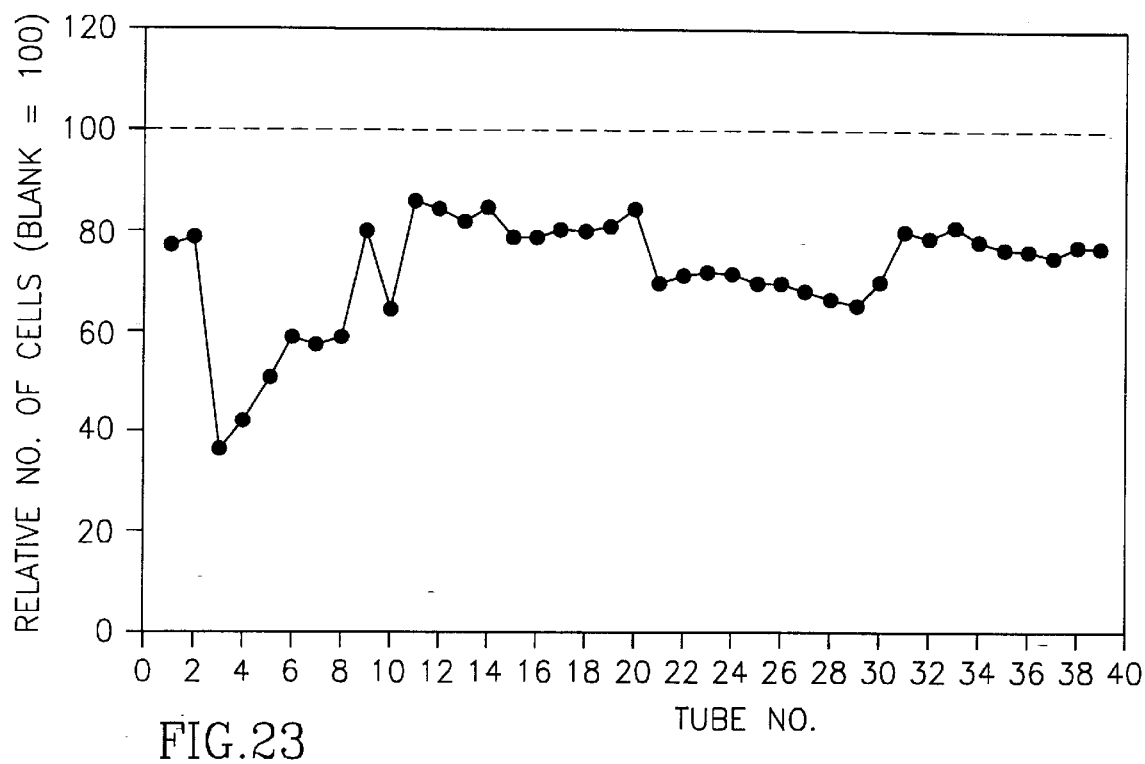
FIG. 23 shows the activity profile of fractions eluted from an analytical RP-HPLC column in inhibiting proliferation of $Nb_2$ cells. The solution fed into the column consisted of active fractions (eluted at 18%–28% acetonitrile) from a preparative RP-HPLC column.

The activity profile of the solution eluted from this column can be seen in FIG. 23. It can be seen that the highest specific inhibition in the CHO aliquot was found in Fractions 2–8, although a secondary inhibitory peak cam also be seen in Fraction 10. Some weak activity can also be observed in a wide peak in Fractions 21–30.

8. Purification of MF 8.1 Procedure

A method was developed for purification of MF consisting of the following steps:

(a) Preparation of a conditioned medium:

The conditioned medium is prepared from the L-8 cell in PBS as described under 1.1.2.

(b) Ultrafiltration:

The condition medium is subjected to ultrafiltration through a membrane with a molecular cut-off of 3,000 Daltons, as described under 2.

(c) Preparative RP-HPLC

The 3,000 Dalton ultrafiltrate is then chromatographed on a preparative RP-HPLC, C - 18 column. Typically the column is first washed with HPLC grade water for 20 mins., then 200 ml of the 3,000 Dalton ultrafiltrate are loaded onto the column and washing with water continues for a further 10 min, period. The column is then developed with an acetonitrile: water gradient between 0% acetonitrile to 60% acetonitrile over a 30 min. period. The rate of the running fluid is about 100 ml/min. The active fractions elute at fractions ensuing from the column between about 8–14 mins.

The active fractions are then pooled together and the pooled fraction is then concentrated in a rotary evaporator (Rotovap™, Büchi, Switzerland) followed by a concentrating centrifuge.

(d) Analytical RP-HPLC.

The pooled concentrated and dried fraction is then dissolved in 5 ml water, dried again in vacuum and then dissolved in 2 ml water. 1 ml of this concentrated fraction is then chromatographed graphed in an analytical RP-HPLC, C - 18 column with the running fluid being a acetonitrile:water gradient, between 0% acetonitrile to 60% acetonitrile over a 20 min. period with a flow rate of 1 ml/min. The column is loaded and then washed with water for 5 mins. Following this washing, the column is developed with the acetonitrile gradient.

The active fraction elute at fractions ensuing from the column between 12–19 mins.

The active fractions are then concentrated and dried in a concentrated centrifuge.

(e) Size exclusion chromatography:

The dried fractions are then mixed with formic acid and the 200 ml samples of this solution are then loaded onto the size exclusion column described under 7.6.4, the developing fluid and the running conditions being also as described there. The active fractions elute primarily after 27–32 mins.

It should be noted that different columns even such having similar specifications to those mentioned above, and slight variations in the elution conditions, may yield different elution profiles and accordingly active fractions may be eluted after different retention times to the ones reported above. However, by testing each fraction for inhibitory activity as described above, it will be possible to the artisan, without any undue difficulty to locate and isolate the purified fractions containing the GR of the invention.

8.2 Purification results

Figure 24:
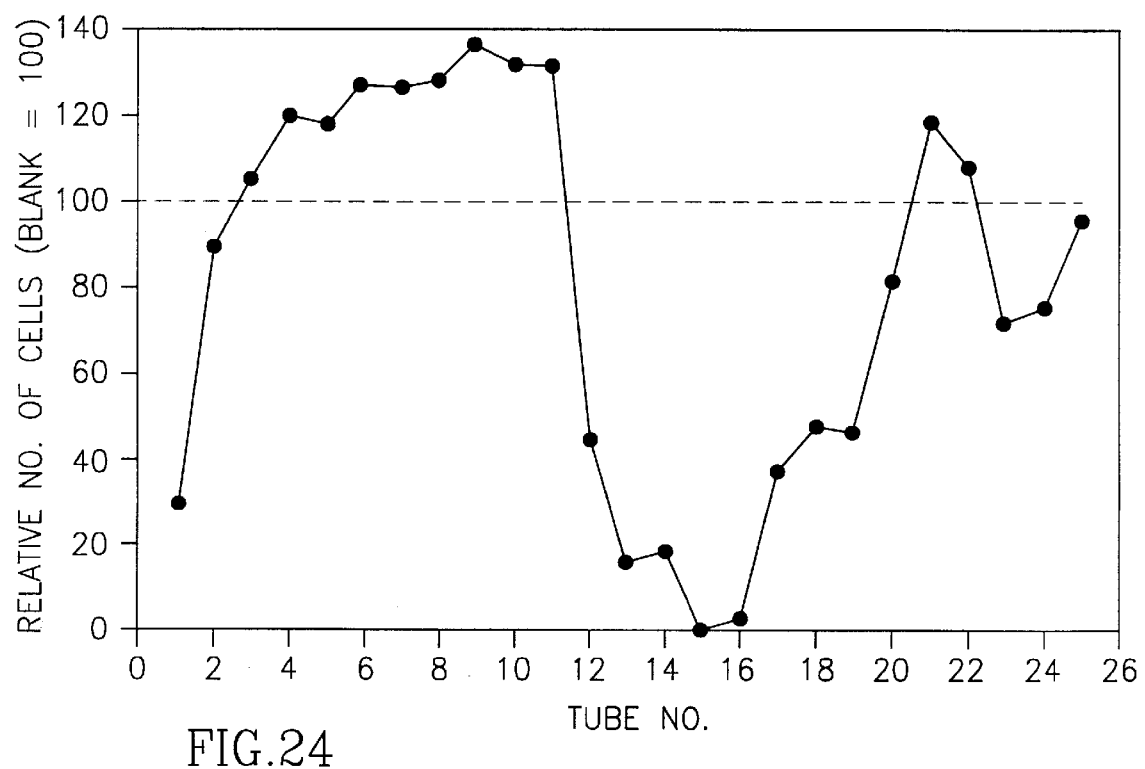
FIG. 24 shows the activity profile of fractions eluted from a size exclusion column in inhibiting proliferation of $Nb_2$ cells. The solutions fed into the column were Fractions 13–17 from the aliquot shown in FIG. 23.

FIG. 24 shows the inhibitory activity profile of fractions eluted from an analytical RP-HPLC and activity of fractions eluted from a size exclusion HPLC (FIG. 25), the purification procedure being as described above in Section 8.1.

9. NMR—possible oligosaccharide nature of MF

Figure 25:
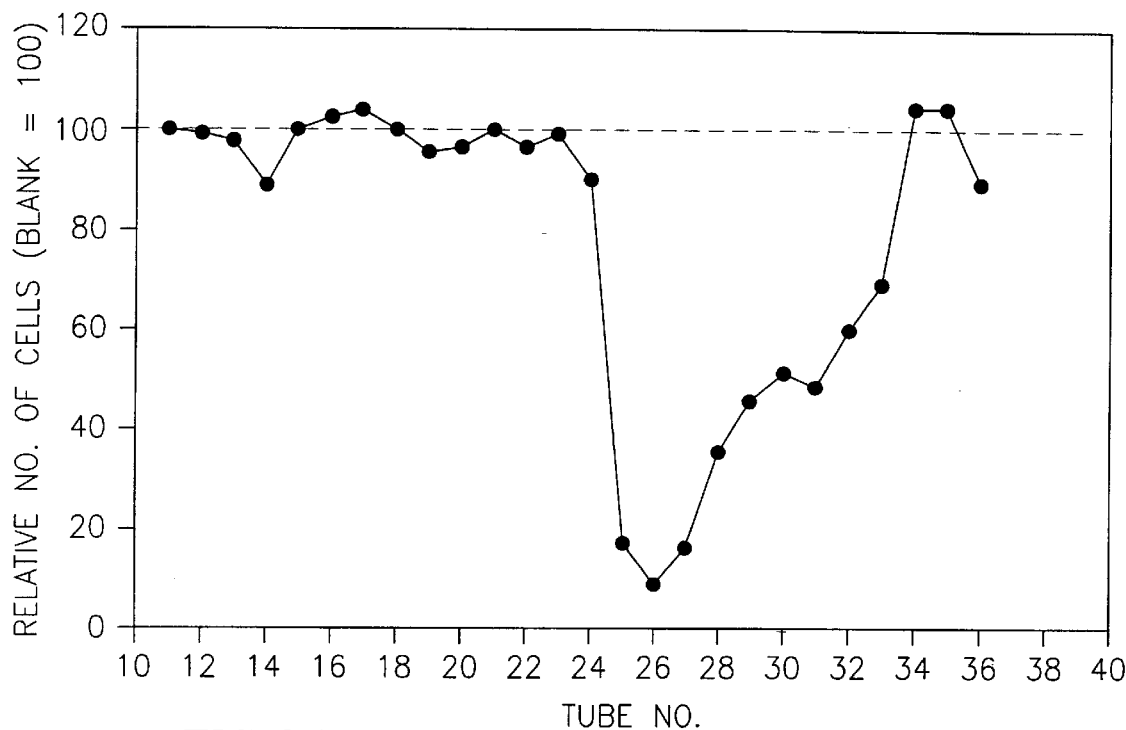
FIG. 25 shows the activity profile of various fractions eluted from a hydrophilic interaction (CHO) column, inhibiting proliferation of $Nb_2$ cells. Solutions fed into the column were pooled Fractions 27–30 from the aliquot shown in FIG. 24.

Active fractions eluted from size exclusion column such as tat shown in FIG. 25, were dried and then dissolved in methanol (there were 3 consecutive cycles of drying and then dissolution in methanol). The methanol extract was then evaporated to dryness, and the preparation was redissolved in 0.5 ml of Deutero methanol. The remainder after the methanol extraction was dissolved in 0.5 ml of Deutero water.

Figure 26:
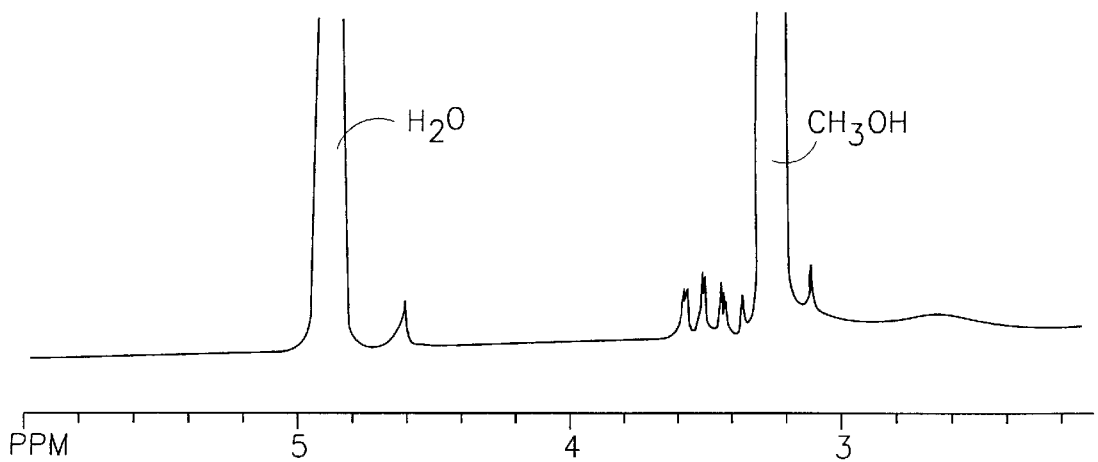
FIGS. 26 shows an NMR scan of active fractions obtained from a size exclusion column (fractions eluted between 27–32 mins.).

The NMR spectrum can be seen in FIG. 26. As can be seen, the NMR scan of the water fraction shows one, probably insignificant peak whereas the NMR scan of the methanol extract showed several peaks at a field of 3–4 ppm. These peaks are characteristic of protons of C—OH groups, typical of oligosaccharides.

These results suggest a possibility that MF is an oligosaccharide.

10. Activity of 3,000 Dalton ultrafiltrate of white blood cells CM and fractionation thereof A 3,000 Dalton ultrafiltrate obtained from white blood cells CM was tested for activity and compared to that of a 3,000 Dalton ultrafiltrate from L-8 CM. The results are shown in the following Table V:

TABLE V

| Tested medium | Amount (ml) | Inhibition % |
|---|---|---|
| 3,000 Dalton ultrafiltrate at L-8 CM | 0.4 | 43 |
|  | 0.3 | 29 |
|  | 0.2 | 11 |
|  | 0.1 | 0 |
| 3,000 Dalton ultrafiltrate of white blood cells CM | 0.4 | 32 |
|  | 0.3 | 21 |
|  | 0.2 | 17 |
|  | 0.1 | 6 |

200 ml of the 3,000 Dalton ultrafiltrate from the white blood cells CM were separated on a preparative RP-HPLC as described above (see Section 7.6.6). Fractious of 200 ml were collected. Aliquots of 10 (out of 200) ml were dried and dissolved in 0.6 ml. 0.1 ml thereafter was applied into each well.

For comparison, 3,000 Dalton ultrafiltrate from the L-8 CM was fractionated in the same manner.

Results are shown in the following Table VI:

TABLE VI

| Fraction No. | % Inhibition | |
|---|---|---|
|  | WBF[1] | MF[2] |
| 2 | 4 | 22 |
| 3 | 5 | 25 |
| 4 | 30 | 47 |
| 5 | 28 | 58 |
| 6 | 21 | 45 |
| 7 | 2 | 33 |

[1] 3,000 Dalton ultrafiltrate of white blood cell CM
[2] 3,000 Dalton ultrafiltrate of L-8 cells As can be seen, both aliquots shows an inhibitory peak in Fractions 4–6.

We claim:

1. A low molecular weight endogenous growth regulator (LMW-EGR) obtainable from a process comprising the steps:

(a) culturing white blood cells or muscle cells in a growth medium;
  (b) separating the cells from the medium; and
  (c) collecting LMW-EGR from the supernatant;
    said LMW-EGR being biologically active in inhibiting the proliferation of cells and has the following additional characteristics:
      molecular weight of less than about 3000 Daltons, water soluble, heat stable, and non-proteinaceous.

2. LMW-EGR according to claim 1, being biologically active in inhibiting proliferation of tumor cells, without substantially affecting proliferation of non-tumorous cells.

3. LMW-EGR according to claim 1, being biologically active in inhibiting proliferation of tumor cells, without substantially affecting proliferation of bone marrow cells.

4. LMW-EGR according to claim 1, being biologically active in inhibiting proliferation of lymphoma cells, without substantially affecting proliferation of non-tumorous lymphocytes.

5. LMW-EGR according to claim 1, having a molecular weight below about 2,000 Daltons.

6. LMW-EGR according to claim 1, having a molecular weight of about 500 Daltons.

7. LMW-EGR according to claim 1, wherein said LMW-EGR is secreted or shed by a rat muscle cell line designated L-8 and which is deposited in the American Type Culture Collection (ATCC) under designation CRL 1769.

8. A composition comprising a therapeutically effective amount of LMW-EGR according to claim 1, together with a pharmaceutically acceptable carrier or diluent.

9. A composition comprising a therapeutically effective amount of LMW-EGR according to claim 7, together with a pharmaceutically acceptable carrier or diluent.

10. A composition according to claim 8, for oral administration.

11. A method for diagnosing an individual's cancerous state, or for determining risk of an individual to develop cancer, comprising:

(a) obtaining a test fluid, which is either a body fluid from the individual, or a supernatant from a culture of cells withdrawn from said individual;
  (b) determining the level of LMW-EGR, as recited in claim 1, in the test fluid;
  (c) comparing said level to an average level of said LMW-EGR in healthy individuals, a level below average being an indication either that said individual has cancer or is of a high risk of developing cancer.

12. A process for the obtention of a low molecular weight endogenous growth regulator (LMW-EGR), comprising:

(a) growing cells under conditions in which the cells produce, secrete or shed cell growth regulator into their surrounding medium;
  (b) collecting supernatant of the cell culture;
  (c) separating between a fraction of the supernatant comprising substances of a molecular weight above about 3,000 Daltons and a fraction of the supernatant comprising substances of a molecular weight below about 3,000 Daltons, and selecting the latter. wherein the LMW-EGR inhibits proliferation of tumor cells, has a molecular weight of less than about 3,000 Daltons, is water soluble, heat stable, and non-proteinaceous.

13. A process according to claim 12, further including the step:

(d) subjecting the selected fraction to chromatographic purification procedures.

14. A process according to claim 13, further including the step:

(e) rechromatographing the selected fractions obtained in step (d) through an RP-HPLC column and selecting fractions which exhibit growth inhibitory activity on tumor cells.

15. A process according to claim 13, further including the step:
(e) chromatographing the selected fractions obtained in step (d) by size exclusion chromatography and selecting fractions which exhibit growth inhibitory activity on tumor cells.

16. A process for the recovery of a low molecular weight endogenous growth regulator (LMW-EGR), comprising:
(a) culturing muscle cells or white blood cells;
(b) collecting supernatant from the cell culture;
(c) filtering the supernatant through a membrane having a molecular cut-off of below about 3,000 Daltons;
(d) chromatographing the filtrate obtained in (c) through a reverse phase high pressure liquid chromatography (RP-HPLC) column and selecting fractions which exhibit growth inhibitory activity on tumor cells, wherein the LMW-EGR inhibits proliferation of tumor cells, has a molecular weight of less than about 3,000 Daltons, is water soluble, heat stable, and non-proteinaceous.

17. Cell growth regulator obtainable by the process of claim 15.

18. Cell growth regulator obtainable by the process of claim 12.

19. Cell growth regulator obtainable by the process of claim 13.

20. Cell growth regulator obtainable by the process of claim 14.

* * * * *